(12) United States Patent
Jacquel et al.

(10) Patent No.: US 12,357,194 B2
(45) Date of Patent: Jul. 15, 2025

(54) INFORMATIVE DISPLAY FOR NON-CONTACT PATIENT MONITORING

(71) Applicant: Covidien LP, Mansfield, MA (US)

(72) Inventors: Dominique Jacquel, Edinburgh (GB); Paul S. Addison, Edinburgh (GB)

(73) Assignee: Covidien LP, Mansfield, MA (US)

( * ) Notice: Subject to any disclaimer, the term of this patent is extended or adjusted under 35 U.S.C. 154(b) by 1020 days.

(21) Appl. No.: 17/303,219

(22) Filed: May 24, 2021

(65) Prior Publication Data

US 2022/0007966 A1    Jan. 13, 2022

Related U.S. Application Data

(60) Provisional application No. 63/057,413, filed on Jul. 28, 2020, provisional application No. 63/049,889, filed on Jul. 9, 2020.

(51) Int. Cl.
  *A61B 5/08*     (2006.01)
  *A61B 5/00*     (2006.01)
  *A61B 5/087*    (2006.01)

(52) U.S. Cl.
  CPC .......... *A61B 5/0826* (2013.01); *A61B 5/0077* (2013.01); *A61B 5/087* (2013.01); *A61B 5/743* (2013.01)

(58) Field of Classification Search
  None
  See application file for complete search history.

(56) References Cited

U.S. PATENT DOCUMENTS

| | | |
|---|---|---|
| 5,107,845 A | 4/1992 | Guern et al. |
| 5,408,998 A | 4/1995 | Mersch |
| 5,704,367 A | 1/1998 | Ishikawa et al. |
| 5,800,360 A | 9/1998 | Kisner et al. |
| 5,995,856 A | 11/1999 | Mannheimer et al. |

(Continued)

FOREIGN PATENT DOCUMENTS

| | | |
|---|---|---|
| CA | 2234191 A1 | 10/1998 |
| CN | 106725410 A | 5/2017 |

(Continued)

OTHER PUBLICATIONS

Amazon, "Dockem Koala Tablet Wall Mount Dock for iPad Air/Mini/Pro, Samsung Galaxy Tab/Note, Nexus 7/10, and More (Black Brackets, Screw-in Version)", https://www.amazon.com/Tablet-Dockem-Samsung-Brackets-Version-dp/B00JV75FC6?th=1, First available Apr. 22, 2014, viewed on Nov. 16, 2021, Apr. 22, 2014, 4 pages.

(Continued)

*Primary Examiner* — Rene T Towa
*Assistant Examiner* — Matthew Eric Ogles
(74) *Attorney, Agent, or Firm* — Draft Masters IP, LLC

(57) ABSTRACT

Described herein are various embodiments of an informative display that may be used in conjunction with non-contact patient monitoring systems and methods. The informative display may include one or more patient data images providing historical and real time data relating the patient being monitored by the non-contact patient monitoring system. The patient data images may be configured to display visualizations of various patient events, such as low flow, apnea, and/or patient movement.

20 Claims, 16 Drawing Sheets

(56) References Cited

U.S. PATENT DOCUMENTS

| | | |
|---|---|---|
| 6,241,684 B1 | 6/2001 | Amano et al. |
| 6,668,071 B1 | 12/2003 | Minkin et al. |
| 6,920,236 B2 | 7/2005 | Prokoski |
| 7,431,700 B2 | 10/2008 | Aoki et al. |
| 7,558,618 B1 | 7/2009 | Williams |
| 8,149,273 B2 | 4/2012 | Liu et al. |
| 8,754,772 B2 | 6/2014 | Horng et al. |
| 8,792,969 B2 | 7/2014 | Bernal et al. |
| 8,971,985 B2 | 3/2015 | Bernal et al. |
| 9,226,691 B2 | 1/2016 | Bernal et al. |
| 9,282,725 B2 | 3/2016 | Jensen-Jarolim et al. |
| 9,301,710 B2 | 4/2016 | Mestha et al. |
| 9,402,601 B1 | 8/2016 | Berger et al. |
| 9,436,984 B2 | 9/2016 | Xu et al. |
| 9,443,289 B2 | 9/2016 | Xu et al. |
| 9,504,426 B2 | 11/2016 | Kyal et al. |
| 9,508,141 B2 | 11/2016 | Khachaturian et al. |
| 9,607,138 B1 | 3/2017 | Baldwin et al. |
| 9,662,022 B2 | 5/2017 | Kyal et al. |
| 9,693,693 B2 | 7/2017 | Farag et al. |
| 9,693,710 B2 | 7/2017 | Mestha et al. |
| 9,697,599 B2 | 7/2017 | Prasad et al. |
| 9,750,461 B1 | 9/2017 | Telfort |
| 9,839,756 B2 | 12/2017 | Klasek |
| 9,943,371 B2 | 4/2018 | Bresch et al. |
| 10,213,540 B2 | 2/2019 | Burbank et al. |
| 10,278,585 B2 | 5/2019 | Ferguson et al. |
| 10,376,147 B2 | 8/2019 | Wood et al. |
| 10,398,353 B2 | 9/2019 | Addison et al. |
| 10,447,972 B2 | 10/2019 | Patil |
| 10,489,912 B1 | 11/2019 | Brailovskiy |
| 10,523,852 B2 | 12/2019 | Tzvieli et al. |
| 10,588,779 B2 | 3/2020 | Vorhees et al. |
| 10,589,916 B2 | 3/2020 | Mcrae |
| 10,650,585 B2 | 5/2020 | Kiely |
| 10,667,723 B2 | 6/2020 | Jacquel et al. |
| 10,702,188 B2 | 7/2020 | Addison et al. |
| 10,729,357 B2 | 8/2020 | Larson et al. |
| 10,874,331 B2 | 12/2020 | Kaiser et al. |
| 10,937,296 B1 | 3/2021 | Kukreja et al. |
| 10,939,824 B2 | 3/2021 | Addison et al. |
| 10,939,834 B2 | 3/2021 | Khwaja et al. |
| 10,966,059 B1 | 3/2021 | Dayal et al. |
| 11,311,252 B2 | 4/2022 | Jacquel et al. |
| 11,315,275 B2 | 4/2022 | Addison et al. |
| 11,317,828 B2 | 5/2022 | Addison et al. |
| 11,350,850 B2 | 6/2022 | Jacquel et al. |
| 11,850,026 B2 | 12/2023 | Levi et al. |
| 2002/0137464 A1 | 9/2002 | Dolgonos et al. |
| 2004/0001633 A1 | 1/2004 | Caviedes |
| 2004/0258285 A1 | 12/2004 | Hansen et al. |
| 2005/0203348 A1 | 9/2005 | Shihadeh et al. |
| 2007/0116328 A1 | 5/2007 | Sablak et al. |
| 2008/0001735 A1 | 1/2008 | Tran |
| 2008/0108880 A1 | 5/2008 | Young et al. |
| 2008/0279420 A1 | 11/2008 | Masticola et al. |
| 2008/0295837 A1 | 12/2008 | McCormick et al. |
| 2009/0024012 A1 | 1/2009 | Li et al. |
| 2009/0050155 A1* | 2/2009 | Alder ............... A61M 16/06 128/204.23 |
| 2009/0141124 A1 | 6/2009 | Liu et al. |
| 2009/0304280 A1 | 12/2009 | Aharoni et al. |
| 2010/0152600 A1* | 6/2010 | Droitcour ........... A61B 5/7221 600/534 |
| 2010/0210924 A1 | 8/2010 | Parthasarathy et al. |
| 2010/0236553 A1 | 9/2010 | Jafari et al. |
| 2010/0249630 A1 | 9/2010 | Droitcour et al. |
| 2010/0324437 A1 | 12/2010 | Freeman et al. |
| 2011/0144517 A1 | 6/2011 | Cervantes |
| 2011/0150274 A1 | 6/2011 | Patwardhan et al. |
| 2012/0065533 A1 | 3/2012 | Carrillo et al. |
| 2012/0075464 A1 | 3/2012 | Derenne |
| 2012/0195473 A1 | 8/2012 | De Haan et al. |
| 2012/0243797 A1 | 9/2012 | Di Venuto Dayer et al. |
| 2013/0073312 A1 | 3/2013 | Thompson et al. |
| 2013/0267873 A1 | 10/2013 | Fuchs |
| 2013/0271591 A1 | 10/2013 | Van Leest et al. |
| 2013/0272393 A1 | 10/2013 | Kirenko et al. |
| 2013/0275873 A1 | 10/2013 | Shaw et al. |
| 2013/0324830 A1 | 12/2013 | Bernal et al. |
| 2013/0324876 A1 | 12/2013 | Bernal et al. |
| 2014/0023235 A1 | 1/2014 | Cennini et al. |
| 2014/0052006 A1 | 2/2014 | Lee et al. |
| 2014/0053840 A1 | 2/2014 | Liu |
| 2014/0073860 A1 | 3/2014 | Urtti |
| 2014/0139405 A1 | 5/2014 | Ribble et al. |
| 2014/0140592 A1 | 5/2014 | Lasenby et al. |
| 2014/0235976 A1 | 8/2014 | Bresch et al. |
| 2014/0267718 A1 | 9/2014 | Govro et al. |
| 2014/0272860 A1 | 9/2014 | Peterson et al. |
| 2014/0275832 A1 | 9/2014 | Muehlsteff et al. |
| 2014/0276104 A1 | 9/2014 | Tao et al. |
| 2014/0330336 A1 | 11/2014 | Errico et al. |
| 2014/0334697 A1 | 11/2014 | Kersten et al. |
| 2014/0358017 A1 | 12/2014 | Op Den Buijs et al. |
| 2014/0378810 A1 | 12/2014 | Davis et al. |
| 2014/0379369 A1 | 12/2014 | Kokovidis et al. |
| 2015/0003723 A1 | 1/2015 | Huang et al. |
| 2015/0068069 A1 | 3/2015 | Tran et al. |
| 2015/0094597 A1 | 4/2015 | Mestha et al. |
| 2015/0131880 A1 | 5/2015 | Wang et al. |
| 2015/0157269 A1 | 6/2015 | Lisogurski et al. |
| 2015/0198707 A1 | 7/2015 | Al-Alusi |
| 2015/0223731 A1 | 8/2015 | Sahin |
| 2015/0238150 A1 | 8/2015 | Subramaniam |
| 2015/0265187 A1 | 9/2015 | Bernal et al. |
| 2015/0282724 A1 | 10/2015 | McDuff et al. |
| 2015/0286779 A1 | 10/2015 | Bala et al. |
| 2015/0301590 A1 | 10/2015 | Furst et al. |
| 2015/0317814 A1 | 11/2015 | Johnston et al. |
| 2015/0379370 A1 | 12/2015 | Clifton et al. |
| 2016/0000335 A1 | 1/2016 | Khachaturian et al. |
| 2016/0049094 A1 | 2/2016 | Gupta et al. |
| 2016/0082222 A1 | 3/2016 | Garcia Molina et al. |
| 2016/0140828 A1 | 5/2016 | Deforest |
| 2016/0143598 A1 | 5/2016 | Rusin et al. |
| 2016/0151022 A1 | 6/2016 | Berlin et al. |
| 2016/0156835 A1 | 6/2016 | Ogasawara et al. |
| 2016/0174887 A1 | 6/2016 | Kirenko et al. |
| 2016/0189518 A1* | 6/2016 | Krüger ............... A61B 5/091 340/573.1 |
| 2016/0210747 A1 | 7/2016 | Hay et al. |
| 2016/0235344 A1 | 8/2016 | Auerbach |
| 2016/0310084 A1 | 10/2016 | Banerjee et al. |
| 2016/0317041 A1 | 11/2016 | Porges et al. |
| 2016/0345931 A1 | 12/2016 | Xu et al. |
| 2016/0367186 A1 | 12/2016 | Freeman et al. |
| 2017/0007342 A1 | 1/2017 | Kasai et al. |
| 2017/0007795 A1 | 1/2017 | Pedro et al. |
| 2017/0055877 A1 | 3/2017 | Niemeyer |
| 2017/0065484 A1 | 3/2017 | Addison et al. |
| 2017/0071516 A1 | 3/2017 | Bhagat et al. |
| 2017/0095215 A1 | 4/2017 | Watson et al. |
| 2017/0095217 A1 | 4/2017 | Hubert et al. |
| 2017/0119340 A1 | 5/2017 | Nakai et al. |
| 2017/0147772 A1 | 5/2017 | Meehan et al. |
| 2017/0164904 A1 | 6/2017 | Kirenko |
| 2017/0172434 A1 | 6/2017 | Amelard et al. |
| 2017/0173262 A1 | 6/2017 | Veltz |
| 2017/0238805 A1 | 8/2017 | Addison et al. |
| 2017/0238842 A1 | 8/2017 | Jacquel et al. |
| 2017/0311887 A1 | 11/2017 | Leussler et al. |
| 2017/0319114 A1 | 11/2017 | Kaestle |
| 2018/0042486 A1 | 2/2018 | Yoshizawa et al. |
| 2018/0042500 A1 | 2/2018 | Liao et al. |
| 2018/0049669 A1* | 2/2018 | Vu ............... A61B 5/0507 |
| 2018/0053392 A1 | 2/2018 | White et al. |
| 2018/0104426 A1 | 4/2018 | Oldfield et al. |
| 2018/0106897 A1 | 4/2018 | Shouldice et al. |
| 2018/0169361 A1 | 6/2018 | Dennis et al. |
| 2018/0217660 A1 | 8/2018 | Dayal et al. |
| 2018/0228381 A1 | 8/2018 | Leboeuf et al. |
| 2018/0303351 A1 | 10/2018 | Mestha et al. |
| 2018/0310844 A1 | 11/2018 | Tezuka et al. |

(56) References Cited

U.S. PATENT DOCUMENTS

| | | |
|---|---|---|
| 2018/0325420 A1 | 11/2018 | Gigi |
| 2018/0333050 A1 | 11/2018 | Greiner et al. |
| 2018/0333102 A1 | 11/2018 | De Haan et al. |
| 2018/0352150 A1 | 12/2018 | Purwar et al. |
| 2019/0050985 A1 | 2/2019 | Den Brinker et al. |
| 2019/0133499 A1 | 5/2019 | Auerbach |
| 2019/0142274 A1 | 5/2019 | Addison et al. |
| 2019/0183383 A1* | 6/2019 | Brayanov ............... G16H 50/30 |
| 2019/0199970 A1 | 6/2019 | Greiner et al. |
| 2019/0209046 A1 | 7/2019 | Addison et al. |
| 2019/0209083 A1 | 7/2019 | Wu et al. |
| 2019/0307365 A1 | 10/2019 | Addison et al. |
| 2019/0311101 A1 | 10/2019 | Nienhouse |
| 2019/0343480 A1 | 11/2019 | Shute et al. |
| 2019/0380599 A1 | 12/2019 | Addison et al. |
| 2019/0380807 A1 | 12/2019 | Addison et al. |
| 2020/0046302 A1 | 2/2020 | Jacquel et al. |
| 2020/0187827 A1 | 6/2020 | Addison et al. |
| 2020/0202154 A1 | 6/2020 | Wang et al. |
| 2020/0205734 A1 | 7/2020 | Mulligan et al. |
| 2020/0237225 A1 | 7/2020 | Addison et al. |
| 2020/0242790 A1 | 7/2020 | Addison et al. |
| 2020/0250406 A1 | 8/2020 | Wang et al. |
| 2020/0253560 A1 | 8/2020 | De Haan |
| 2020/0279464 A1 | 9/2020 | Llewelyn |
| 2020/0289024 A1 | 9/2020 | Addison et al. |
| 2020/0329976 A1 | 10/2020 | Chen et al. |
| 2020/0409383 A1 | 12/2020 | Maunder |
| 2021/0068670 A1 | 3/2021 | Redtel |
| 2021/0142874 A1 | 5/2021 | Llewelyn |
| 2021/0153746 A1 | 5/2021 | Addison et al. |
| 2021/0201517 A1 | 7/2021 | Yang et al. |
| 2021/0233631 A1 | 7/2021 | Llewelyn |
| 2021/0235992 A1 | 8/2021 | Addison |
| 2021/0295662 A1 | 9/2021 | Bugbee et al. |
| 2021/0313075 A1 | 10/2021 | McNamara et al. |
| 2022/0211296 A1 | 7/2022 | Addison et al. |
| 2023/0122367 A1 | 4/2023 | Tesar |

FOREIGN PATENT DOCUMENTS

| | | |
|---|---|---|
| CN | 111728602 A | 10/2020 |
| CN | 112233813 A | 1/2021 |
| DE | 19741982 A1 | 10/1998 |
| EP | 2793189 B1 | 11/2016 |
| EP | 2428162 B1 | 8/2017 |
| EP | 3207862 A1 | 8/2017 |
| EP | 3207863 A1 | 8/2017 |
| EP | 3384827 A1 | 10/2018 |
| EP | 2772828 B1 | 1/2019 |
| JP | 2004173010 A | 6/2004 |
| JP | 2004283373 A | 10/2004 |
| JP | 3744778 B2 | 12/2005 |
| JP | 2009544080 A | 12/2009 |
| JP | 2011130996 A | 7/2011 |
| KR | 101644843 B1 | 8/2016 |
| RS | 20120373 A1 | 4/2014 |
| WO | 2004100067 A2 | 11/2004 |
| WO | 2005079658 A2 | 9/2005 |
| WO | 2010034107 A1 | 4/2010 |
| WO | 2010036653 A1 | 4/2010 |
| WO | 2015059700 A1 | 4/2015 |
| WO | 2015078735 A1 | 6/2015 |
| WO | 2015110859 A1 | 7/2015 |
| WO | 2016065411 A1 | 5/2016 |
| WO | 2016178141 A1 | 11/2016 |
| WO | 2016209491 A1 | 12/2016 |
| WO | 2017060463 A1 | 4/2017 |
| WO | 2017089139 A1 | 6/2017 |
| WO | 2017100188 A2 | 6/2017 |
| WO | 2017144934 A1 | 8/2017 |
| WO | 2018042376 A1 | 3/2018 |
| WO | 2019094893 A1 | 5/2019 |
| WO | 2019135877 A1 | 7/2019 |
| WO | 2019240991 A1 | 12/2019 |
| WO | 2020033613 A1 | 2/2020 |
| WO | 2021044240 A1 | 3/2021 |

OTHER PUBLICATIONS

Gsmarena, "Apple iPad Pro 11 (2018)", https://www.gsmarena.com/apple_ipad_pro_11_(2018)-9386.pjp, viewed on Nov. 16, 2021, 1 page.

Rezaei, Mahdi, et al., "DeepSOCIAL: Social Distancing Monitoring and Infection Risk Assessment in COVID-19 Pandemic", Applied Sciences, vol. 10, 7514, Oct. 26, 2020, pp. 1-29, 29 pages.

Sathyamoorthy, Adarsh Jagan, et al., "COVID-Robot: Monitoring Social Distancing Constraints in Crowded Scenarios", Aug. 21, 2020, pp. 1-11, 11 pages.

Xinyi, Liu, et al., "An Image Captioning Method for Infant Sleeping Environment Diagnosis", Springer International Publishing, May 15, 2019, pp. 18-26, 9 pages.

Sokooti, Hess, et al., "Hierarchical Prediction of Registration Misalignment Using a Convolutional LSTM: Application to Chest CT Scans", IEEE Access, IEEE, USA, vol. 9, Apr. 20, 2021, 62008-62020, 13 pages.

Al-Naji, Ali, et al., "Real Time Apnoea Monitoring of Children Using the Microsoft Kinect Sensor: A Pilot Study", Sensors, 17(286), Feb. 3, 2017, 15 pages.

Harte, James M., et al., "Chest wall motion analysis in healthy volunteers and adults with cystic fibrosis using a novel Kinect-based motion tracking system", Medical & Biological Engineering & Computing, 54(11), Feb. 13, 2016, pp. 1631-1640, 11 pages.

Mcduff, Daniel J., et al., "A Survey of Remote Optical Photoplethysmographic Imaging Methods", IEEE 987-1-4244-0270-1/15, 2015, pp. 6398-6404, 7 pages.

Mestha, L.K., et al., "Towards Continuous Monitoring of Pulse Rate in Neonatal Intensive Care Unit with a Webcam", Proc. of 36th Annual Int. Conf. of the IEEE Engineering in Medicine and Biology Society, Chicago, IL, 2014, pp. 3817-3820, 4 pages.

Nguyen, et al., "3D shape, deformation and vibration measurements using infrared Kinect sensors and digital image correlation", Applied Optics, vol. 56, No. 32, Nov. 10, 2017, 8 pages.

Ni, et al., "RGBD-Camera Based Get-Up Event Detection for Hospital Fall Prevention", Acoustics, Speech and Signal Processing (ICASSP) 2012 IEEE International Conf., Mar. 2012, pp. 1405-1408, 6 pages.

Nisar, et al., "Contactless heart rate monitor for multiple persons in a video", IEEE International Conference on Consumer Electronics—Taiwan (ICCE-TW), XP03291229 [Retreived on Jul. 25, 2016], May 27, 2016, 2 pages.

Pereira, C., et al., "Noncontact Monitoring of Respiratory Rate in Newborn Infants Using Thermal Imaging", IEEE Transactions on Biomedical Engineering, Aug. 23, 2018, 10 pages.

Poh, et al., "Advancements in Noncontact, Multiparameter Physiological Measurements Using a Webcam", IEEE Transactions on Biomedical Engineering, vol. 58, No. 1, Jan. 2011, pp. 7-11, 5 pages.

Poh, et al., "Non-contact, automated cardiac pulse measurements using video imaging and blind source separation", OPT. Express 18, 2010, pp. 10762-10774, 14 pages.

Povsic, Klemen, et al., "Real-Time 3D visualization of the thoraco-abdominal surface during breathing with body movement and deformation extraction", Physiological Measurement, vol. 36, No. 7, May 28, 2015, pp. 1497-1516, 22 pages.

Prochazka, et al., "Microsoft Kinect Visual and Depth Sensors for Breathing and Heart Rate Analysis", Senors, vol. 16, No. 7, Jun. 28, 2016, 11 pages.

Rajan, V., et al., "Clinical Decision Support for Stroke using Multiview Learning based Models for NIHSS Scores", PAKDD 2016 Workshop: Predictive Analytics in Critical Care (PACC), Auckland, New Zealand, 2016, pp. 190-199, 10 pages.

Rajan, V., et al., "Dependency Clustering of Mixed Data with Gaussian Mixture Copulas", 25th International Joint Conference on Artificial Intelligence IJCAI, New York, USA, 2016, pp. 1967-1973, 7 pages.

(56) References Cited

OTHER PUBLICATIONS

Reisner, A., et al., "Utility of the Photoplethysmogram in Circulatory Monitoring", American Society of Anesthesiologist, May 2008, pp. 950-958, 9 pages.

Rougier, Caroline, et al., "Robust Video Surveillance for Fall Detection Based on Human Shape Deformation", IEEE Transactions on Circuits and Systems for Video Technology, vol. 21, No. 5, May 2011, pp. 611-622, 12 pages.

Rubinstein, M, "Analysis and Visualization of Temporal Variations in Video", Department of Electrical Engineering and Computer Science, Massachusetts Institute of Technology, Feb. 2014, 118 pages.

Scalise, Lorenzo, et al., "Heart rate measurement in neonatal patients using a webcamera", Department of Industrial Engineering and Mathematical Science, Italy, 978-1-4673-0882-3/12, EEE, 2012, 4 pages.

Schaerer, J., et al., "Multi-dimensional respiratory motion tracking from markerless optical surface imaging based on deformable mesh registration", Physics in Medicine and Biology, vol. 57, No. 2, Dec. 14, 2011, pp. 357-373, 18 pages.

Sengupta, A., et al., "A Statistical Model for Stroke Outcome Prediction and Treatment Planning", 38th Annual International Conference of the IEE Engineering in Medicine and Biology (Society IEEE EMBC2016), Orlando, USA, 2016, pp. 2516-2519, 4 pages.

Shah, Nitin, et al., "Performance of three new-generation pulse oximeters during motion and low perfursion in volunteers", Journal of Clinical Anesthesia, No. 24, 2012, pp. 385-391, 7 pages.

Shao, Dangdang, et al., "Noncontact Monitoring Breathing Pattern, Exhalation Flow Rate and Pulse Transit Time", EEE Transactions on Biomedical Engineering, vol. 61, No. 11, Nov. 2014, pp. 2760-2767, 8 pages.

Shrivastava, H., et al., "Classification with Imbalance: A Similarity-based Method for Predicting Respiratory Failure", IEEE International Conference on Bioinformatics and Biomedicine (IEEE BIBM2015), Washington, DC,USA, 2015, pp. 707-714, 8 pages.

Sun, Yu, et al., "Motion-compensated noncontact imaging photoplethysmography to monitor cardiorespiratory status during exercise", Journal of Biomedical Optics, vol. 16, No. 7, Jul. 1, 2011, 10 pages.

Sun, Yu, et al., "Noncontact imaging photoplethysmography to effectively access pulse rate variability", Journal of Biomedical Optics, vol. 18(6), Jun. 2013, 10 pages.

Tamura, et al., "Wearable Photoplethysmographic Sensors—Past & Present", Electronics, vol. 3, 2014, pp. 282-302, 21 pages.

Tarassenko, L., et al., "Non-contact video-based vital sign monitoring using ambient light and auto-regressive models", Institute of Physics and Engineering in Medicine, vol. 35, 2014, pp. 807-831, 26 pages.

Teichmann, D., et al., "Non-Contact monitoring techniques-Principles and applications", In Proc. of IEEE International Conference of the Engineering in Medicine and Biology Society (EMBC), San Diego, CA, 2012, pp. 1302-1305, 4 pages.

Verkruysee, Wim, et al., "Calibration of Contactless Pulse Oximetry", Anesthesia & Analgesia, vol. 124, No. 1, Jan. 2017, pp. 136-145, 10 pages.

Mllarroel, Mauricio, et al., "Continuous non-contact vital sign monitoring in neonatal intensive care unit", Healthcare Technology Letters, vol. 1, Issue 3, 2014, pp. 87-91, 5 pages.

Wadhwa, N., et al., "Phase-Based Video Motion Processing", MIT Computer Science and Artificial Intelligence Lab, Jul. 2013, 9 pages.

Wadhwa, N., et al., "Riesz pyramids for fast phase-based video magnification", In Proc. of IEEE International Conference on Computational Photography (ICCP), Santa Clara, CA, 2014, 10 pages.

Wang, W, et al., "Exploiting spatial redundancy of image sensor for motion robust rPPG", IEEE Transactions on Biomedical Engineering, vol. 62, No. 2, 2015, pp. 415-425, 11 pages.

Wu, H.Y., et al., "Eulerian video magnifcation for revealing subtle changes in the world", ACM Transactions on Graphics (TOG), vol. 31, No. 4, 2012, pp. 651-658, 8 pages.

Wulbrand, H, et al., "Submental and diaphragmatic muscle activity during and at resolution of mixed and obstructive apneas and cardiorespiratory arousal in preterm infants", Pediatric Research, No. 38(3), 1995, pp. 298-305, 9 pages.

Zaunsede, et al., "Spatio-temporal analysis of blood perfusion by imaging photoplethysmography", Progress in Biomedical Optics and Imaging, SPIE—International Society for Optical Engineering, vol. 10501, Feb. 20, 2018, 15 pages.

Zhou, J, et al., "Maximum parsimony analysis of gene copy No. changes in tumor phylogenetics", 15th International Workshop on Algorithms in Bioinformatics WABI 2015, Atlanta, USA, 2015, pp. 108-120, 13 pages.

"European Search Report", European Application No. 17156334.9, Applicant: Covidien LP, Aug. 23, 2017, 10 pages.

"European Search Report", European Patent Application No. 17156337.2, Applicant: Covidien LP, Aug. 23, 2017, 10 pages.

"International Search Report and Written Opinion", International Application No. PCT/US2018/060648, Jan. 28, 2019, 17 pages.

"International Search Report and Written Opinion", International Application No. PCT/US2018/065492, Mar. 8, 2019, 12 pages.

"International Search Report and Written Opinion", International Application No. PCT/US19/035433, Nov. 11, 2019, 17 pages.

"International Search Report and Written Opinion", International Application No. PCT/US2019/045600, Oct. 23, 2019, 19 pages.

"Invitation to Pay Additional Fees and Partial International Search Report", International Application No. PCT/US2019/035433, Sep. 13, 2019, 16 pages.

"Medical Electrical Equipment, Part 2-61: Particular requirements for basic safety and essential performance of pulse oximeter equipment", BSI Standards Publication, BS EN ISO 80601-2-61, 2011, 98 pages.

Aarts, Lonneke A.M., et al., "Non-contact heart rate monitoring utilizing camera photoplethysmography in neonatal intensive care unit—A Pilot Study", Early Human Development 89, 2013, pp. 943-948, 6 pages.

Abbas, A.K., et al., "Neonatal non-contact respiratory monitoring based on real-time infrared thermography", Biomed. Eng. Online, vol. 10, No. 93, 2011, 17 pages.

Addison, Paul S., "A Review of Signal Processing Used in the Implementation of the Pulse Oximetry Photoplethysmographic Fluid Responsiveness Parameter", International Anesthesia Research Society, vol. 119, No. 6, Dec. 2014, pp. 1293-1306, 14 pages.

Addison, Paul S., et al., "Developing an algorithm for pulse oximetry derived respirator rate (RRoxi): a healthy volunteer study", J Clin comput, No. 26, 2012, pp. 45-51, 7 pages.

Addison, Paul S., et al., "Pulse oximetry-derived respiratory rate in general care floor patients", J. Clin Monit Comput, No. 29, 2015, pp. 113-120, 8 pages.

Addison, P.S., et al., "Video-based Heart Rate Monitoring across a Range of Skin Pigmentations during an Acute Hypoxic Challenge", J Clin Monit Comput, vol. 9, Nov. 9, 2017, 15 pages.

Amelard, et al., "Non-contact transmittance photoplethysmographic imaging (PPGI) for long-distance cardiovascular monitoring", ResearchGate, XP055542534 [Retrieved online Jan. 15, 2019], Mar. 23, 2015, pp. 1-13, 14 pages.

Armanian, A. M., "Caffeine administration to prevent apnea in very premature infants", Pediatrics & Neonatology, 57(5), 2016, pp. 408-412, 5 pages.

Barone, S, et al., "Computer-aided modelling of three-dimensional maxillofacial tissues through multi-modal imaging", Proceedings of the Institution of Mechanical Engineers, Journal of Engineering in Medicine, Part H vol. 227, No. 2, Feb. 1, 2013, 1 page.

Barone, S, et al., "Creation of 3D Multi-body Orthodontic Models by Using Independent Imaging Sensors", Senros MDPI AG Switzerland, vol. 13, No. 2, Jan. 1, 2013, pp. 2033-2050, 18 pages.

Bhattacharya, S., et al., "A Novel Classification Method for Predicting Acute Hypotensive Episodes in Critical Care", 5th ACM Conference on Bioinformatics, Computational Bilogy and Health Informatics (ACM-BCB 2014), Newport Beach, USA, 2014, 10 pages.

(56) References Cited

OTHER PUBLICATIONS

Bhattacharya, S. , et al., "Unsupervised learning using Gaussian Mixture Copula models", 21st International Conference on Computational Statistics (COMPSTAT 2014), Geneva, Switzerland, 2014, pp. 523-530, 8 pages.
Bickler, Philip E., et al., "Factors Affecting the Performance of 5 Cerebral Oximeters During Hypoxia in Healthy Volunteers", Society for Technology in Anesthesia, vol. 117, No. 4, Oct. 2013, pp. 813-823, 11 pages.
Bousefsaf, Frederic , et al., "Continuous wavelet filtering on webcam photoplethysmographic signals to remotely assess the instantaneous heart rate", Biomedical Signal Processing and Control 8, 2013, pp. 568-574, 7 pages.
Bruser, C. , et al., "Adaptive Beat-to-Beat Heart Rate Estimation in Ballistocardiograms", IEEE Transactions Information Technology in Biomedicine, vol. 15, No. 5, Sep. 2011, pp. 778-786, 9 pages.
Cennini, Giovanni , et al., "Heart rate monitoring via remote photoplethysmography with motion artifacts reduction", Optics Express, vol. 18, No. 5, Mar. 1, 2010, pp. 4867-4875, 9 pages.
Colantonio, S. , et al., "A smart mirror to promote a healthy lifestyle", Biosystems Engineering. vol. 138, Innovations in Medicine and Healthcare, Oct. 2015, pp. 33-43, 11 pages.
Cooley , et al., "An Alorithm for the Machine Calculation of Complex Fourier Series", Aug. 17, 1964, pp. 297-301, 5 pages.
Di Fiore, J.M. , et al., "Intermittent hypoxemia and oxidative stress in preterm infants", Respiratory Physiology & Neurobiology, No. 266, 2019, pp. 121-129, 25 pages.
Fei, J. , et al., "Thermistor at a distance: unobtrusive measurement of breathing", IEEE Transactions on Biomedical Engineering, vol. 57, No. 4, 2010, pp. 968-998, 11 pages.
Feng, Litong , et al., "Dynamic ROI based on K-means for remote photoplethysmography", IEE International Conference on Accoustics, Speech and Signal Processing (ICASSP), Apr. 2015, pp. 1310-1314, 5 pages.
George , et al., "Respiratory Rate Measurement From PPG Signal Using Smart Fusion Technique", International Conference on Engineering Trends and Science & Humanities (ICETSH-2015), 2015, 5 pages.
Goldman, L.J. , "Nasal airflow and thoracoabdominal motion in children using infrared thermographic video processing", Pediatric Pulmonology, vol. 47, No. 5, 2012, pp. 476-486, 11 pages.
Grimm, T. , et al., "Sleep position classification from a depth camera using bed aligned maps", 23rd International Conference on Pattern Recognition (ICPR), Dec. 2016, pp. 319-324, 6 pages.
Guazzi, Alessandro R., et al., "Non-contact measurement of oxygen saturation with an RGB camera", Biomedical Optics Express, vol. 6, No. 9, Sep. 1, 2015, pp. 3320-3338, 19 pages.
Han, J. , et al., "Visible and infrared image registration in man-made environments employing hybrid visuals features", Pattern Recognition Letters, vol. 34, No. 1, 2013, pp. 42-51, 10 pages.
Huddar, V. , et al., "Predicting Postoperative Acute Respiratory Failure in Critical Care using Nursing Notes and Physiological Signals", 36th Annual International Conference of IEEE Engineering in Medicine and Biology Society (IEEE EMBC 2014), Chicago, USA, 2014, pp. 2702-2705, 4 pages.
Hyvarinen, A. , et al., "Independent Component Analysis: Algorithms and Applications", Neural Networks, vol. 13, No. 4, 2000, pp. 411-430, 31 pages.
Javadi, M. , et al., "Diagnosing Pneumonia in Rural Thailand: Digital Cameras versus Film Digitizers for Chest Radiograph Teleradiology", International Journal of Infectious Disease, 10(2), Mar. 2006, pp. 129-135, 7 pages.
Jopling, M. W., et al., "Issues in the Laboratory Evaluation of Pulse Oximeter Performance", Anesth. Analg., No. 94, 2002, pp. S62-S68, 7 pages.
Kastle, Siegfried W., et al., "Determining the Artifact Sensitivity of Recent Pulse Oximeters During Laboratory Benchmarking", Journal of Clinical Monitoring and Computing, vol. 16, No. 7, 2000, pp. 509-552, 14 pages.
Klaessens, J.H.G.M. , et al., "Non-invasive skin oxygenation imaging using a multi-spectral camera system: Effectiveness of various concentration algorithms applied on human skin", Proc. of SPIE, vol. 7174 717408-1, 2009, 14 pages.
Kong, Lingqin , et al., "Non-contact detection of oxygen saturation based on visible light imaging device using ambient light", Optics Express, vol. 21, No. 15, Jul. 29, 2013, pp. 17646-17471, 8 pages.
Kortelainen, J.M. , et al., "Sleep staging based on signals acquired through bed sensor", IEEE Transactions on Informational Technology in Biomedicine, vol. 14, No. 3, May 2010, pp. 776-785, 10 pages.
Kumar, M. , et al., "Distance PPG: Robust non-contact vital signs monitoring using a camera", Biomedical Optics Express, vol. 6, No. 5, May 1, 2015, 24 pages.
Kwon, Sungjun , et al., "Validation of heart rate extraction using video imaging on a built-in camera system of a smartphone", 34th Annual International Conference of the IEEE EMBS, San Diego, CA, USA, Aug. 28-Sep. 1, 2012, pp. 2174-2177, 4 pages.
Lai, C.J. , et al., "Heated humidified high-flow nasal oxygen prevents intraoperative body temperature decrease in non-intubated thoracoscopy", Journal of Anesthesia, Oct. 15, 2018, 8 pages.
Li , et al., "A Non-Contact Vision-Based System for Respiratory Rate Estimation", IEEE 978-1-4244-7929-0/14, 2014, pp. 2119-2122, 4 pages.
Liu, H. , et al., "A Novel Method Based on Two Cameras for Accurate Estimation of Arterial Oxygen Saturation", BioMedical Engineering Online, vol. 14, No. 52, 2015, 18 pages.
Liu, S. , et al., "In-bed pose estimation: Deep learning with shallow dataset. IEEE journal of translational engineering in health and medicine", IEEE Journal of Translational Engineering in Health and Medicine, No. 7, 2019, pp. 1-12, 12 pages.
Liu, C. , et al., "Motion Magnification", ACM Transactions on Graphics (TOG), vol. 24, No. 3, 2005, pp. 519-526, 8 pages.
Lv , et al., "Class Energy Image Analysis for Video Sensor-Based Gait Recognition: A Review", Sensors, No. 15, 2015, pp. 932-964, 33 pages.
"International Search Report and Written Opinion", International Application No. PCT/US2021/015669, Apr. 12, 2021, 15 pages.
Bartula, M., et al., "Camera-based System for Sontactless Monitoring of Respiration", 2013 35th Annual International Conference of the IEEE Engineering in Medicine and Biology Society (EMBC), Jul. 3, 2013, pp. 2672-2675, 4 pages.
Fischer, et al., "ReMoteCare: Health Monitoring with Streaming Video", OCMB '08, 7th International Conference on Mobile Business, IEEE, Piscataway, NJ,, Jul. 7, 2008, pp. 280-286.
Lawrence, E., et al., "Data Collection, Correlation and Dissemination of Medical Sensor information in a WSN", IEEE 2009 Fifth International Conference on Networking and Services, 978-0-7695-3586-9/09, Apr. 20, 2009, pp. 402-408, 7 pages.
Mukherjee, S., et al., "Patient health management system using e-health monitoring architecture", IEEE, International Advance Computing Conference (IACC), 978-1-4799-2572-8/14, Feb. 21, 2014, pp. 400-405, 6 pages.
Reyes, B.A., et al., "Tidal Volume and Instantaneous Respiration Rate Estimation using a Volumetric Surrogate Signal Acquired via a Smartphone Camera", IEEE Journal of Biomedical and Health Informatics, vol. 21(3), Feb. 25, 2016, pp. 764-777, 15 pages.
Srinivas, J., et al., "A Mutual Authentication Framework for Wireless Medical Sensor Networks", Journal of Medical Systems, 41:80, 2017, pp. 1-19, 19 pages.
Transue, S., et al., "Real-time Tidal Volume Estimation using Iso-surface Reconstruction", 2016 IEEE First International Conference on Connected Health: Applications, Systems and Engineering Technologies (CHASE), Jun. 27, 2016, pp. 209-218, 10 pages.
Yu, M.C., et al., "Noncontact Respiratory Measurement of Volume Change Using Depth Camera", 2012 Annual International Conference of the IEEE Engeineering in Medicine and Biology Society, Aug. 28, 2012, pp. 2371-2374, 4 pages.

\* cited by examiner

INFORMATIVE DISPLAY FOR NON-CONTACT PATIENT MONITORING

CROSS-REFERENCE TO RELATED APPLICATION(S)

The present application claims priority under 35 U.S.C. § 119(e) to U.S. Provisional Patent Application No. 63/049,889, entitled "Informative Display for Non-Contact Patient Monitoring" and filed Jul. 9, 2020 and U.S. Provisional Patent Application No. 63/057,413, entitled "Informative Display for Non-Contact Patient Monitoring" and filed Jul. 28, 2020, both of which are incorporated herein by reference in their entirety.

U.S. Patent Application Publication Nos. 2019/0209046 and 2020/0046302 are incorporated herein by reference in their entirety.

TECHNICAL FIELD

The present disclosure relates to informative displays for non-contact patient monitoring, and more specifically, to informative displays for visualizing, e.g., low flow, apnea and/or patient motion events. Various patient breathing parameters can be obtained and/or calculated from depth measurements taken by a non-contact patient monitoring system including a depth sensing camera. The informative display can provide multiple visualizations of low flow, apnea, motion, etc., which can be adaptive such that the visualizations adjust based on further patient breathing measurements.

BACKGROUND

Depth sensing technologies have been developed that, when integrated into non-contact patient monitoring systems, can be used to determine a number of physiological and contextual parameters, such as respiration rate, tidal volume, minute volume, etc. Such parameters can be displayed on a display so that a clinician is provided with a basic visualization of these parameters. For example, respiratory volume as a function of time can be displayed as a rolling line plot to visualize a patient's breathing patterns.

However, additional effort and analysis is required for the clinician to decipher and interpret what the displayed data means with respect to the health of the patient being monitored. Accordingly, a need exists for systems and methods that are capable of both synthesizing patient monitoring data and providing additional visualization of the analyzed data for quick and easy interpretation and identification of developing medical issues.

BRIEF DESCRIPTION OF THE DRAWINGS

Many aspects of the present disclosure can be better understood with reference to the following drawings. The components in the drawing are not necessarily to scale. Instead, emphasis is placed on illustrating clearly the principles of the present disclosure. The drawings should not be taken to limit the disclosure to the specific embodiments depicted but are for explanation and understanding only.

DETAILED DESCRIPTION

Figure 1:
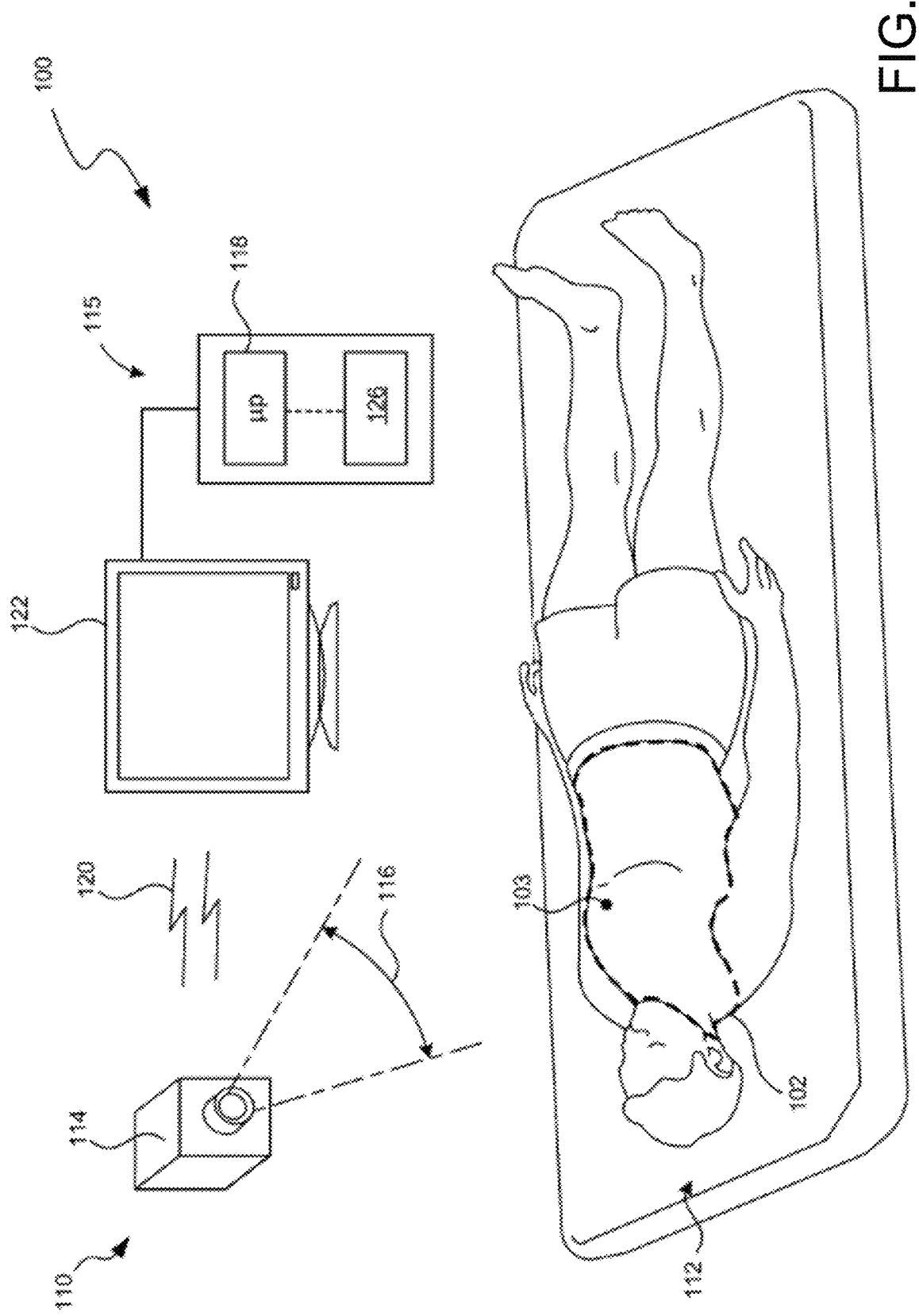
FIG. 1 is a schematic view of a video-based patient monitoring system configured in accordance with various embodiments of the present technology.

The present disclosure relates to informative displays for non-contact patient monitoring. The technology described herein can be incorporated into systems and methods for non-contact patient monitoring. As described in greater detail below, the described technology can include obtaining respiratory volume data, such as via non-contact patient monitoring using depth sensing cameras, and displaying the respiratory volume data as a function of time using a line plot. The technology may further include calculating absolute respiratory flow values from the plot line and determining when the calculated absolute respiratory flow value falls below a predetermined respiratory flow value, at which point a visual flag may be added to the display in order to indicate, e.g., low flow and/or apnea in the monitored patient. Subsequently collected data regarding respiratory volume and absolute respiratory flow values calculated therefrom may alter and/or remove previous visual flags added to the display. In some embodiments, the plot line is visually changed from a first plot line design to a second plot line design when the absolute respiratory flow value falls below the predetermined respiratory flow value to thereby indicate a low flow occurrence. In some embodiments, if the absolute respiratory flow value remains below the predetermined respiratory flow value for longer than a predetermined period of time, the rolling plot line is visually changed from the second plot line design to a third plot line design to thereby indicate an apnea event. In some embodiments, if the absolute respiratory flow value remains below the predetermined respiratory flow value for shorter than the predetermined period of time, the rolling plot line is changed from the second plot line design to the first plot line design and any previous visualization of low flow via use of the second plot line design is removed from the display.

Informative displays presenting patient monitoring data such as respiratory volume as a function of time, a histogram of breathing rates, respiration rate as function of time, and a patient depth image can also be visually altered to easily and quickly convey to a clinician various information pertaining to, e.g., apnea or patient motion events. In some embodiments, detected apnea events are visualized on an informative display by at least one of: adding an apnea label to a patient depth image; visually changing the plot line design of a rolling plot line for respiratory volume as a function of time; dropping to zero a rolling plot line for respiration rate as a function of time; and introducing and/or growing an apnea bar to a histogram of breathing rates. In some embodiments, detected patient motion events are visualized on an informative display by at least one of: adding a motion label to a patient depth image; visually changing the plot line design of a rolling plot line for respiratory volume as a function of time (including the use of a different plot line design than the plot line design used for denoting apnea); dropping to zero or otherwise holding flat a rolling plot line for respiration rate as a function of time; and introducing and growing a new motion bar to a histogram of breathing rates. The informative display may also incorporate the use of visual and/or auditory warnings when detected apnea and/or motion events continue for longer than a predetermined period of time. The informative display may incorporate either or both of the previously described apnea visualizations and motion visualizations.

Specific details of several embodiment of the present technology are described herein with reference to FIGS. 1-12. Although many of the embodiments are described with respect to devices, systems, and methods for video-based monitoring of breathing in a human patient and associated display of this monitoring, other applications and other embodiments in addition to those described herein are within the scope of the present technology. For example, at least some embodiments of the present technology can be useful for video-based monitoring of breathing in other animals and/or in non-patients (e.g., elderly or neonatal individuals within their homes). It should be noted that other embodiments in addition to those disclosed herein are within the scope of the present technology. Further, embodiments of the present technology can have different configurations, components, and/or procedures than those shown or described herein. Moreover, a person of ordinary skill in the art will understand that embodiments of the present technology can have configurations, components, and/or procedures in addition to those shown or described herein and that these and other embodiments can be without several of the configurations, components, and/or procedures shown or described herein without deviating from the present technology.

FIG. 1 is a schematic view of a patient 112 and a video-based patient monitoring system 100 configured in accordance with various embodiments of the present technology. The system 100 includes a non-contact detector 110 and a computing device 115. In some embodiments, the detector 110 can include one or more image capture devices, such as one or more video cameras. In the illustrated embodiment, the non-contact detector 110 includes a video camera 114. The non-contact detector 110 of the system 100 is placed remote from the patient 112. More specifically, the video camera 114 of the non-contact detector 110 is positioned remote from the patient 112 in that it is spaced apart from and does not contact the patient 112. The camera 114 includes a detector exposed to a field of view (FOV) 116 that encompasses at least a portion of the patient 112.

The camera 114 can capture a sequence of images over time. The camera 114 can be a depth sensing camera, such as a Kinect camera from Microsoft Corp. (Redmond, Washington) or Intel camera such as the D415, D435, and SR305 cameras from Intel Corp, (Santa Clara, California). A depth sensing camera can detect a distance between the camera and objects within its field of view. Such information can be used to determine that a patient 112 is within the FOV 116 of the camera 114 and/or to determine one or more regions of interest (ROI) to monitor on the patient 112. Once a ROI is identified, the ROI can be monitored over time, and the changes in depth of regions (e.g., pixels) within the ROI 102 can represent movements of the patient 112 associated with breathing. As described in greater detail in U.S. Patent Application Publication No. 2019/0209046, those movements, or changes of regions within the ROI 102, can be used to determine various breathing parameters, such as tidal volume, minute volume, respiratory rate, respiratory, etc. Those movements, or changes of regions within the ROI 102, can also be used to detect various breathing abnormalities, as discussed in greater detail in U.S. Patent Application Publication No. 2020/0046302. The various breathing abnormalities can include, for example, low flow, apnea, rapid breathing (tachypnea), slow breathing, intermittent or irregular breathing, shallow breathing, obstructed and/or impaired breathing, and others. U.S. Patent Application Publication Nos. 2019/0209046 and 2020/0046302 are incorporated herein by reference in their entirety.

In some embodiments, the system 100 determines a skeleton-like outline of the patient 112 to identify a point or points from which to extrapolate a ROI. For example, a skeleton-like outline can be used to find a center point of a chest, shoulder points, waist points, and/or any other points on a body of the patient 112. These points can be used to determine one or more ROIs. For example, a ROI 102 can be defined by filling in area around a center point 103 of the chest, as shown in FIG. 1. Certain determined points can define an outer edge of the ROI 102, such as shoulder points. In other embodiments, instead of using a skeleton, other points are used to establish a ROI. For example, a face can be recognized, and a chest area inferred in proportion and spatial relation to the face. In other embodiments, a reference point of a patient's chest can be obtained (e.g., through a previous 3-D scan of the patient), and the reference point can be registered with a current 3-D scan of the patient. In these and other embodiments, the system 100 can define a ROI around a point using parts of the patient 112 that are within a range of depths from the camera 114. In other words, once the system 100 determines a point from which to extrapolate a ROI, the system 100 can utilize depth information from the depth sensing camera 114 to fill out the ROI. For example, if the point 103 on the chest is selected, parts of the patient 112 around the point 103 that are a similar depth from the camera 114 as the point 103 are used to determine the ROI 102.

In another example, the patient 112 can wear specially configured clothing (not shown) that includes one or more features to indicate points on the body of the patient 112, such as the patient's shoulders and/or the center of the patient's chest. The one or more features can include visually encoded message (e.g., bar code, QR code, etc.), and/or brightly colored shapes that contrast with the rest of the patient's clothing. In these and other embodiments, the one or more features can include one or more sensors that are configured to indicate their positions by transmitting light or other information to the camera 114. In these and still other embodiments, the one or more features can include a grid or another identifiable pattern to aid the system 100 in recognizing the patient 112 and/or the patient's movement. In some embodiments, the one or more features can be stuck on the clothing using a fastening mechanism such as adhesive, a pin, etc. For example, a small sticker can be placed on a patient's shoulders and/or on the center of the patient's chest that can be easily identified within an image captured by the camera 114. The system 100 can recognize the one or more features on the patient's clothing to identify specific points on the body of the patient 112. In turn, the system 100 can use these points to recognize the patient 112 and/or to define a ROI.

In some embodiments, the system 100 can receive user input to identify a starting point for defining a ROI. For example, an image can be reproduced on a display 122 of the system 100, allowing a user of the system 100 to select a patient 112 for monitoring (which can be helpful where multiple objects are within the FOV 116 of the camera 114) and/or allowing the user to select a point on the patient 112 from which a ROI can be determined (such as the point 103 on the chest of the patient 112). In other embodiments, other methods for identifying a patient 112, identifying points on the patient 112, and/or defining one or more ROI's can be used.

Figure 2:
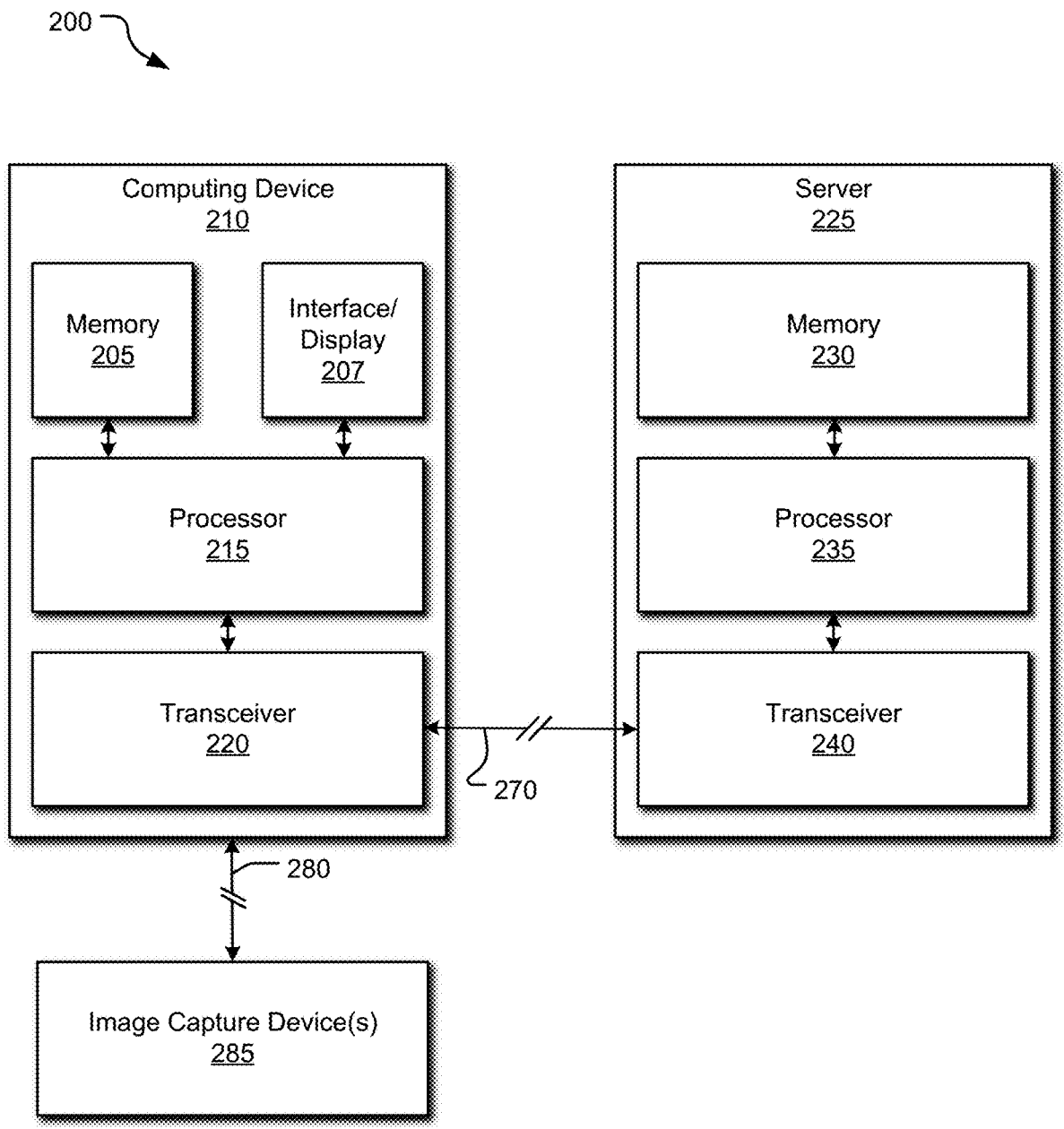
FIG. 2 is a block diagram illustrating a video-based patient monitoring system having a computing device, a server, and one or more image capturing devices, and configured in accordance with various embodiments of the present technology.

The images detected by the camera 114 can be sent to the computing device 115 through a wired or wireless connection 120. The computing device 115 can include a processor 118 (e.g., a microprocessor), the display 122, and/or hardware memory 126 for storing software and computer instructions. Sequential image frames of the patient 112 are recorded by the video camera 114 and sent to the processor 118 for analysis. The display 122 can be remote from the camera 114, such as a video screen positioned separately from the processor 118 and the memory 126. Other embodiments of the computing device 115 can have different, fewer, or additional components than shown in FIG. 1. In some embodiments, the computing device 115 can be a server. In other embodiments, the computing device 115 of FIG. 1 can be additionally connected to a server (e.g., as shown in FIG. 2 and discussed in greater detail below). The captured images/video can be processed or analyzed at the computing device 115 and/or a server to determine a variety of parameters (e.g., tidal volume, minute volume, respiratory rate, etc.) of a patient's breathing. In some embodiments, some or all of the processing may be performed by the camera, such as by a processor integrated into the camera or when some or all of the computing device 115 is incorporated into the camera.

FIG. 2 is a block diagram illustrating a video-based patient monitoring system 200 (e.g., the video-based patient monitoring system 100 shown in FIG. 1) having a computing device 210, a server 225, and one or more image capture devices 285, and configured in accordance with various embodiments of the present technology. In various embodiments, fewer, additional, and/or different components can be used in the system 200. The computing device 210 includes a processor 215 that is coupled to a memory 205. The processor 215 can store and recall data and applications in the memory 205, including applications that process information and send commands/signals according to any of the methods disclosed herein. The processor 215 can also (i) display objects, applications, data, etc. on an interface/display 207 and/or (ii) receive inputs through the interface/display 207. As shown, the processor 215 is also coupled to a transceiver 220.

The computing device 210 can communicate with other devices, such as the server 225 and/or the image capture device(s) 285 via (e.g., wired or wireless) connections 270 and/or 280, respectively. For example, the computing device 210 can send to the server 225 information determined about a patient from images captured by the image capture device(s) 285. The computing device 210 can be the computing device 115 of FIG. 1. Accordingly, the computing device 210 can be located remotely from the image capture device(s) 285, or it can be local and close to the image capture device(s) 285 (e.g., in the same room). In various embodiments disclosed herein, the processor 215 of the computing device 210 can perform the steps disclosed herein. In other embodiments, the steps can be performed on a processor 235 of the server 225. In some embodiments, the various steps and methods disclosed herein can be performed by both of the processors 215 and 235. In some embodiments, certain steps can be performed by the processor 215 while others are performed by the processor 235. In some embodiments, information determined by the processor 215 can be sent to the server 225 for storage and/or further processing.

In some embodiments, the image capture device(s) 285 are remote sensing device(s), such as depth sensing video camera(s), as described above with respect to FIG. 1. In some embodiments, the image capture device(s) 285 can be or include some other type(s) of device(s), such as proximity sensors or proximity sensor arrays, heat or infrared sensors/cameras, sound/acoustic or radio wave emitters/detectors, or other devices that include a field of view and can be used to monitor the location and/or characteristics of a patient or a region of interest (ROI) on the patient. Body imaging technology can also be utilized according to the methods disclosed herein. For example, backscatter x-ray or millimeter wave scanning technology can be utilized to scan a patient, which can be used to define and/or monitor a ROI. Advantageously, such technologies can be able to "see" through clothing, bedding, or other materials while giving an accurate representation of the patient's skin. This can allow for more accurate measurements, particularly if the patient is wearing baggy clothing or is under bedding. The image capture device(s) 285 can be described as local because they are relatively close in proximity to a patient such that at least a part of a patient is within the field of view of the image capture device(s) 285. In some embodiments, the image capture device(s) 285 can be adjustable to ensure that the patient is captured in the field of view. For example, the image capture device(s) 285 can be physically movable, can have a changeable orientation (such as by rotating or panning), and/or can be capable of changing a focus, zoom, or other characteristic to allow the image capture device(s) 285 to adequately capture images of a patient and/or a ROI of the patient. In various embodiments, for example, the image capture device(s) 285 can focus on a ROI, zoom in on the ROI, center the ROI within a field of view by moving the image capture device(s) 285, or otherwise adjust the field of view to allow for better and/or more accurate tracking/measurement of the ROI.

The server 225 includes a processor 235 that is coupled to a memory 230. The processor 235 can store and recall data and applications in the memory 230. The processor 235 is also coupled to a transceiver 240. In some embodiments, the processor 235, and subsequently the server 225, can communicate with other devices, such as the computing device 210 through the connection 270.

The devices shown in the illustrative embodiment can be utilized in various ways. For example, either the connections 270 and 280 can be varied. Either of the connections 270 and 280 can be a hard-wired connection. A hard-wired connection can involve connecting the devices through a USB (universal serial bus) port, serial port, parallel port, or other type of wired connection that can facilitate the transfer of data and information between a processor of a device and a second processor of a second device. In another embodiment, either of the connections 270 and 280 can be a dock where one device can plug into another device. In other embodiments, either of the connections 270 and 280 can be a wireless connection. These connections can take the form of any sort of wireless connection, including, but not limited to, Bluetooth connectivity, Wi-Fi connectivity, infrared, visible light, radio frequency (RF) signals, or other wireless protocols/methods. For example, other possible modes of wireless communication can include near-field communications, such as passive radio-frequency identification (RFID) and active RFID technologies. RFID and similar near-field communications can allow the various devices to communicate in short range when they are placed proximate to one another. In yet another embodiment, the various devices can connect through an internet (or other network) connection. That is, either of the connections 270 and 280 can represent several different computing devices and network components that allow the various devices to communicate through the internet, either through a hard-wired or wireless connection. Either of the connections 270 and 280 can also be a combination of several modes of connection.

The configuration of the devices in FIG. 2 is merely one physical system 200 on which the disclosed embodiments can be executed. Other configurations of the devices shown can exist to practice the disclosed embodiments. Further, configurations of additional or fewer devices than the devices shown in FIG. 2 can exist to practice the disclosed embodiments. Additionally, the devices shown in FIG. 2 can be combined to allow for fewer devices than shown or can be separated such that more than the three devices exist in a system. It will be appreciated that many various combinations of computing devices can execute the methods and systems disclosed herein. Examples of such computing devices can include other types of medical devices and sensors, infrared cameras/detectors, night vision cameras/detectors, other types of cameras, augmented reality goggles, virtual reality goggles, mixed reality goggle, radio frequency transmitters/receivers, smart phones, personal computers, servers, laptop computers, tablets, blackberries, RFID enabled devices, smart watch or wearables, or any combinations of such devices.

Referring back to FIG. 1, the display 122 can be used to display various information regarding the patient 112 monitored by the system 100. In some embodiments, the system 100, including the video camera 114, the computing device 115 and the processor 118, is used to obtain depth measurements and use those depth measurements to calculate respiratory volume values as described in greater detail in U.S. Patent Application Publication No. 2019/0209046. The calculated respiratory volume values can then be displayed on the display 122, such as on a graph displayed on the display 122 and in which the respiratory volume value is displayed as a function of time via a plot line.

Figure 3:
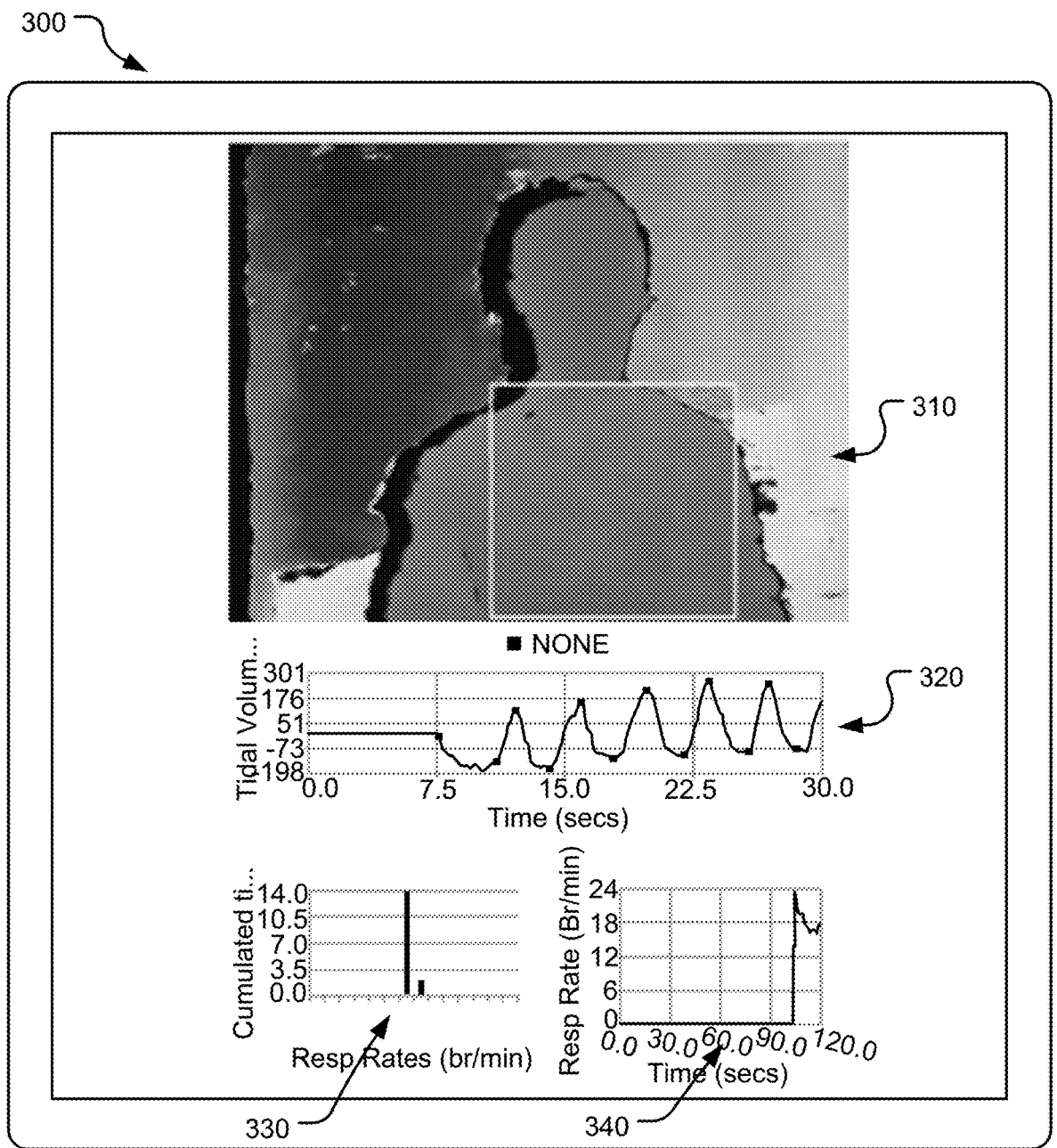
FIG. 3 is a display view for a video-based patient monitoring system configured in accordance with various embodiments of the present technology.

FIG. 3 provides an exemplary (though non-limiting) display 300 in which the display 300 includes a patient depth image 310, a graph 320 detailing respiratory volume as a function of time, a histogram 330 for tracking quantity of parameters such a various breathing rate ranges, and a trend display 340 showing respiratory rate as a function of time. The display 300 may include any combination of these images, including adding additional images not discussed herein or omitting images discussed previously.

Figure 4:
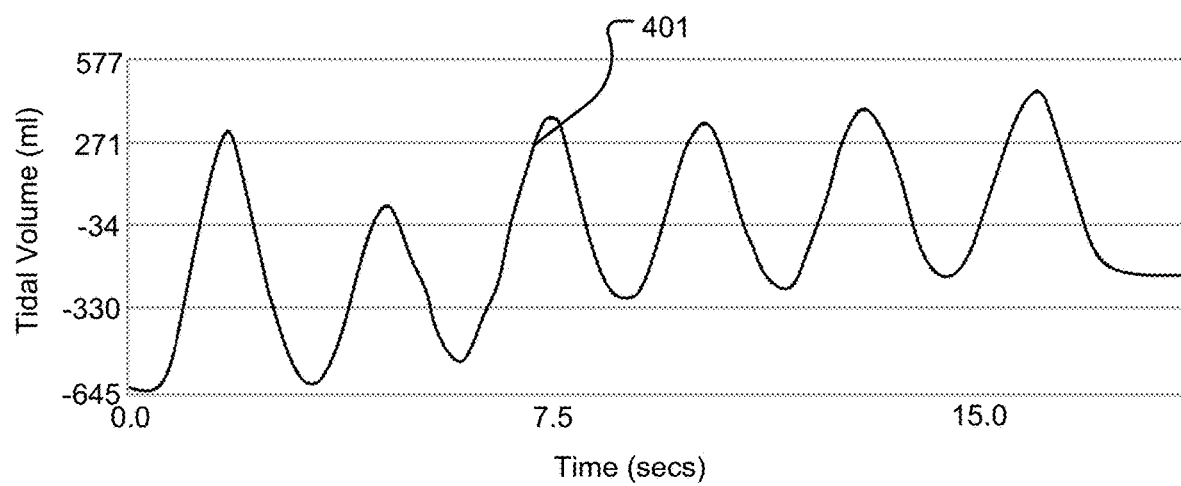
FIG. 4 is a line plot illustrating respiratory volume as a function of time generated using a video-based patient monitoring system configured in accordance with various embodiments of the present technology.

FIG. 4 provides an expanded view of graph 320 showing calculated respiratory volume as a function of time, including a rolling plot line 401. The respiratory volume data can, in some embodiments, be obtained by integrating the change in depths across the patient's chest region. The plot line 401 in FIG. 4 generally shows a modulated waveform, indicating normal breathing by the patient. In order to obtain respiratory flow values, the derivative of the plot line 401 is used. Generally speaking, any slope in the plot line 401, whether positive or negative, indicates some degree of respiratory flow, and therefore respiratory flow values obtained from the plot line 401 can be converted to absolute respiratory flow lines for sake of further analysis and use in identifying and visualizing potential breathing events.

In some embodiments, the absolute respiratory flow value used for identifying and visualizing breathing events (as discussed in greater detail below) is an average of absolute respiratory flow values taken over a set period of time. The set period of time used for calculating an average respiratory flow values is not limited. In some embodiments, the set period of time is one second to thereby provide a one second average respiratory flow value, while in other embodiments, the set period of time is three seconds to thereby provide a three second average respiratory flow value. Some embodiments of the technology described herein may also calculate, for example, both a one second and three second average and use both value in creating an informative display. As noted previously, these averages can be used when determining whether breathing events may be occurring, such as comparing the average respiratory flow value against a predetermined respiratory flow value below which a breathing event is likely to be occurring.

Figure 5A:
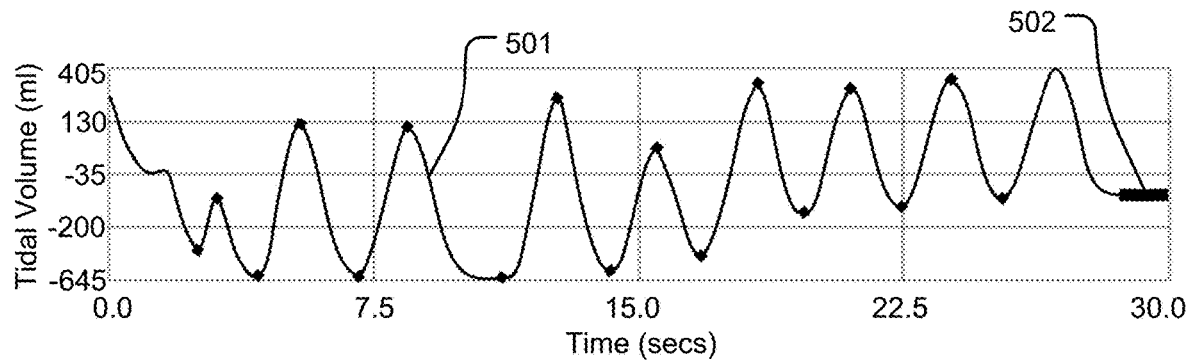
FIGS. 5A-5C are sequential views of a line plot illustrating respiratory volume as a function of time and including visualizations showing low flow flags configured in accordance with various embodiments of the present technology.
Figure 5B:
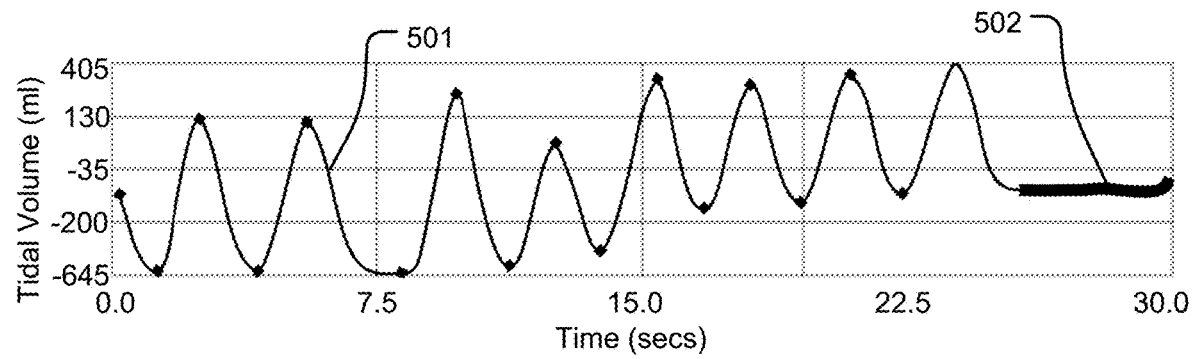
Figure 5C:
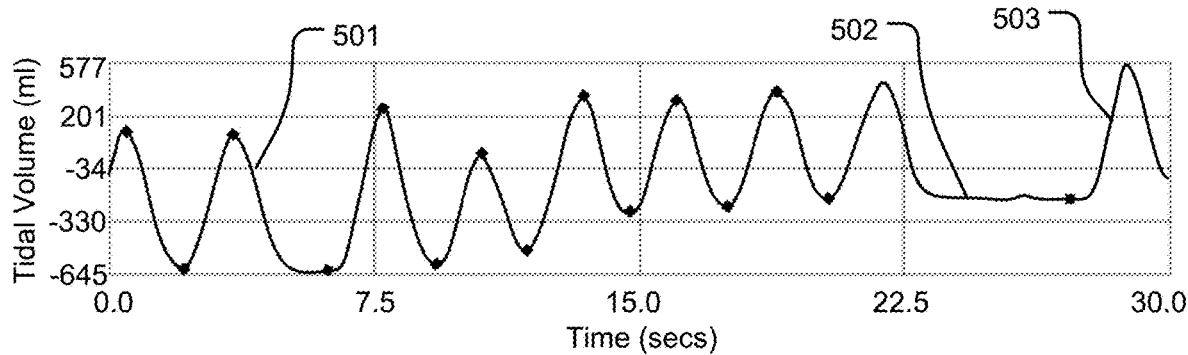

With reference to FIGS. 5A-5C, a sequence of line plots visually altered to highlight an identified potential low flow event are illustrated. FIG. 5A is an extension of FIG. 4 showing additional respiratory volume measurements added to the rolling plot line 501. As these additional data points are added to the plot line 501 and as additional absolute respiratory flow values are derived from the plot line 501, continuous comparison of the absolute respiratory flow value (which as noted above, may be an average respiratory flow value) against a predetermined respiratory flow value is carried out to identify potential breathing events. Generally speaking, instances where the plot line flattens out to close to a horizontal line (indicating close to zero slope value) present potential breathing events, such as low flow and/or apnea, since the flat plot line suggests no inhaling or exhaling by the monitored patient. Accordingly, in some embodiments, the predetermined respiratory flow value against which the absolute respiratory flow value is compared can be a value close to zero, such as 0.25, 0.2, 0.1, or 0.05. As shown in FIG. 5A at plot line section 502, the plot line 501 has flattened close to horizontal, meaning the absolute respiratory flow value has dropped to a value close to or equal to zero. In FIG. 5A, this absolute respiratory flow value is below the predetermined respiratory flow value and as a result, the visual design of the plot line 501 at plot line section 502 is changed from a first design (a thin red line in the case of FIG. 5A) to a second plot line design (a thicker orange line in the case of FIG. 5A). The second plot line design is used to denote a low flow event in the monitored patient based on the absolute respiratory flow value being below the predetermined respiratory flow value. This change in plot line design begins at the time when the absolute respiratory flow value first falls below the predetermined respiratory flow value and provides the clinician with a clear visual representation of the start of a low flow event. While FIGS. 5A-5C use a thin red line for the first plot line design and a thicker orange line for the second plot line design, it should be appreciated that any combination of color, line thickness, pattern, etc., can be used for the different plot line designs.

As shown in FIG. 5B, the plot line section 502 remains generally flat as additional respiratory volume data is collected and added to the graph, indicating an absolute respiratory flow value that continues to be close to or at zero and below the predetermined respiratory flow value. As such, the plot line section 502 remains in the second plot line design, denoting to a clinician a continued low flow event.

In some embodiments, the amount of time during which the absolute respiratory flow value remains below the predetermined respiratory flow value is monitored. In such embodiments, a predetermined period of time is established as a benchmark after which the low flow event can be considered as an apnea event due to its duration where little to no respiratory flow is detected. Any predetermined period of time can be used, and the predetermined period of time may be fixed or dynamic. In a fixed scenario, a fixed period of time is used for all comparisons regardless of any previous data collected from the patient. For example, the fixed period of time may be 5 seconds, 7 seconds, 10 seconds, or more, but the selected fixed predetermined period of time does not change. In a dynamic scenario, previous data collected from the patient being monitored may be used to establish the specific time period assigned to the predetermined period of time. Any suitable previously collected data regarding the patient can be used to adjust the dynamic predetermined period of time. For example, in some embodiments, the dynamic predetermined period of time is based on the average breath duration over a set number of breaths immediately preceding the breathing event. A multiplier can also be used to increase or decrease the predetermined time period calculated based on breathing data taken from a period of time immediately preceding the breathing event. In one non-limiting example, the predetermined period of time may be based on the average breath duration of the three breaths immediately preceding the breathing event. In an example where the average breath duration of the three breaths preceding the breathing event is 4 seconds, this time period can be multiplied by, for example, 0.5, 1.0, 1.5, 2.0, 5.0, etc., to establish a predetermined period of time for this specific breathing event of 2, 4, 6, 8, 20, etc., seconds. In another non-limiting example of a dynamic predetermined period of time, the predetermined period of time may be set as a multiple of the typical exhalation period (from peak to trough of each breath). Use of a dynamic predetermined time period helps to ensure that the low flow and apnea flags are more tailored to the specific patient being monitored and their breathing tendencies.

FIG. 5C illustrates the scenario in which the absolute respiratory flow value does not remain below the predetermined respiratory flow value for longer than the predetermined period of time. As shown in FIG. 5C, the respiratory volume begins to increase at plot line section 503 after a flat period at plot line section 502. Because the plot line at plot line section 503 has a positive slope, the absolute respiratory flow value for that section increases above the predetermined respiratory flow value, signaling the end of a breathing event. Furthermore, because duration of the flat plot line section 502 did not exceed the predetermined period of time, the breathing event previously considered a low flow event does not rise to the level of being considered an apnea event, and therefore is no longer in need of special visualization on the graph. As such, the second plot line design previously used on plot line section 502 is removed from the display and the portion of the plot line (i.e., plot line section 502) between the initial time when the absolute respiratory flow value fell below the predetermined respiratory flow value and the time when the absolute respiratory flow value rose back above the predetermined flow value returns to the first plot line design.

While not shown in FIGS. 5A-5C, in an alternate embodiment, the plot line section 502 remains in the second plot line design even after the plot line rises at plot line section 503 prior to exceeding the predetermined period of time. While the breathing event did not rise to the level of an apnea event, the occurrence of a low flow event may still be of interest to a clinician, and retaining plot line section 502 in the second plot line design can help to provide the clinician with an easy-to-read visualization of this event.

Figure 6A:
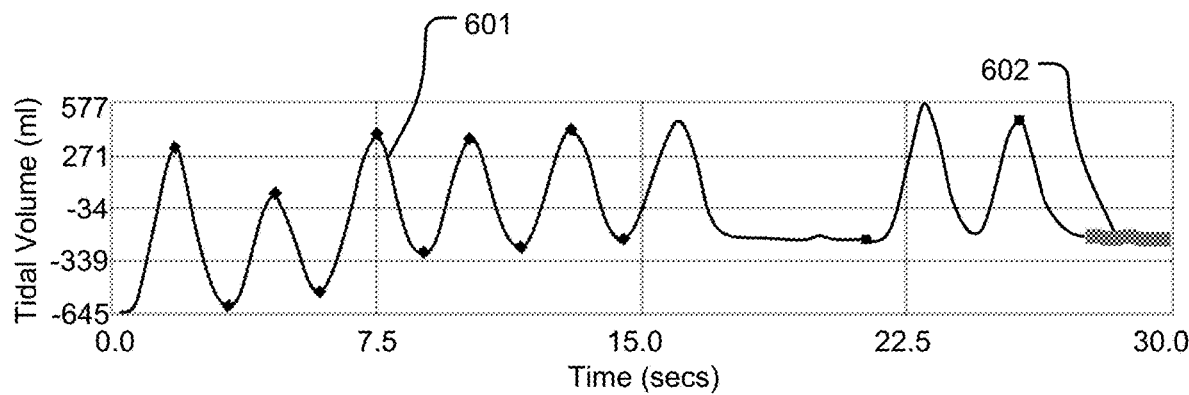
FIGS. 6A-6D are sequential views of a line plot illustrating respiratory volume as a function of time and including visualizations showing apnea flags configured in accordance with various embodiments of the present technology.
Figure 6B:
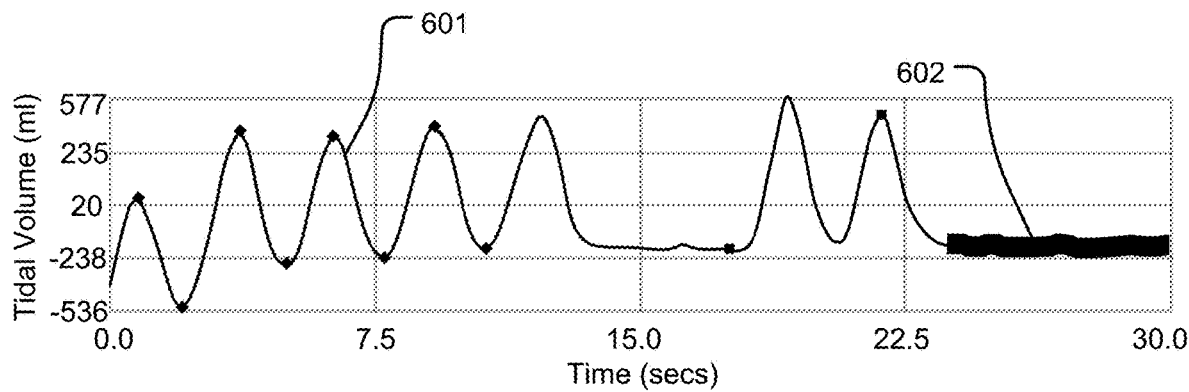

FIGS. 6A-6D illustrate a scenario similar to FIG. 5A-5C, but where the time period that the absolute respiratory flow value remains below the predetermined respiratory flow value exceeds the predetermined period of time. FIG. 6A is similar to FIG. 5B wherein the absolute respiratory flow value has dropped below the predetermined respiratory flow value for a period of time and the plot line section 602 has therefore been visually changed to the second plot line design. However, unlike in the scenario illustrated in FIGS. 5A-5C, FIG. 6B illustrates a scenario in which absolute respiratory flow value remains below the predetermined respiratory flow value for longer than the predetermined period of time. In this event, plot line section 602 which was previously presented in the second plot line design is visually changed to a third plot line design used to denote an apnea event. While FIG. 6B illustrates the third plot line design as being a thicker red line, it should be appreciated that any combination of color, line thickness, shading, etc. can be used for the third plot line design.

As also shown in FIG. 6B, the plot line section 602 is visually changed such that the entirety of the section 602 (i.e., all the way back to the initial time when the absolute respiratory flow value fell below the predetermined respiratory flow value) is visually converted to the third plot line design. In this embodiment, any use of the second plot line design is removed, as the entirety of the section 602 is presented in the third plot line design since the entirety of this time period where the absolute respiratory flow value is below the predetermined respiratory flow value is now considered part of the apnea event.

While not shown in the Figures, in an alternate embodiment, the second plot line design at the first portion of the plot line section 602 can be retained rather than being overwritten by the third plot line design. In such an embodiment, the plot line section 602 would have a portion from the initial time when the absolute respiratory flow value fell below the predetermined respiratory flow value to the time when the absolute respiratory flow value remained below the predetermined respiratory flow value for the predetermined period of time that is in the second plot line design, and a portion after the predetermined period of time that is in the third plot line design. This representation would therefore show the clinician the progression of the breathing event from a low flow event to an apnea event.

Figure 6C:
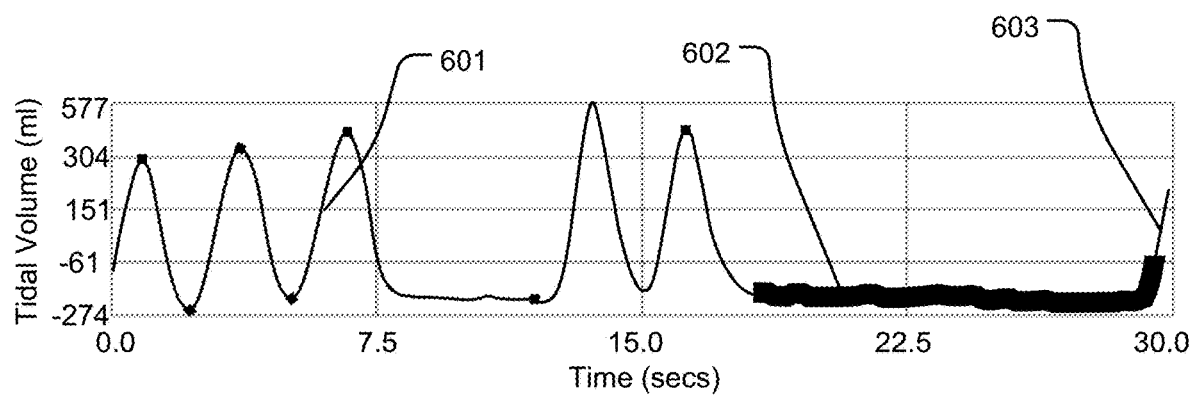

With reference to FIG. 6C, additional respiratory volume data is added to the graph in which the respiratory volume remains flat, and for this entire portion of time, the plot line section 602 retains the third plot line design. However, once the respiratory volume begins to increase upon the resumption of breath by the monitored patient and the absolute respiratory flow value consequently increases above the predetermined respiratory flow value, the plot line section 603 (i.e., the portion of the plot line after the absolute respiratory flow value increases back above the predetermined respiratory flow value) is visually changed back to the first plot line design. The plot line section 602 in the third plot line design, however, is retained to create a historical visual presentation of the apnea event.

Figure 6D:
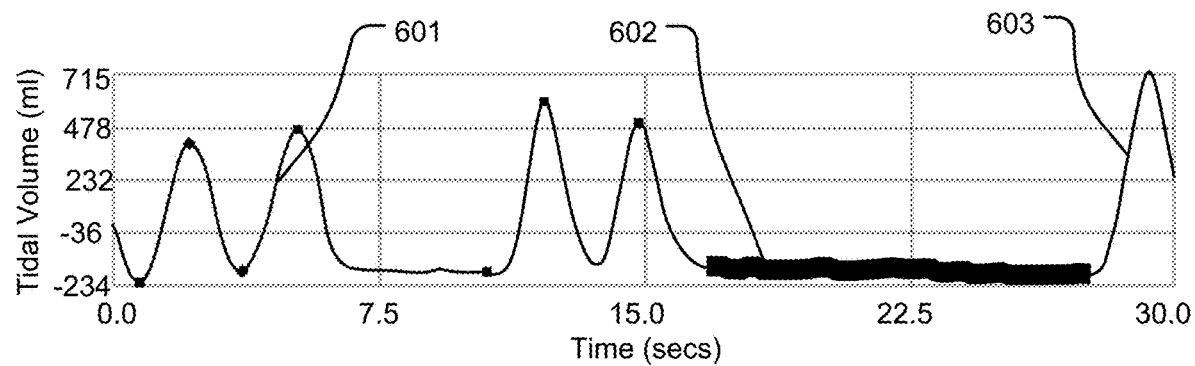

As also shown in FIG. 6C, a scenario may occur wherein the respiratory volume may begin to increase, but because of the use of, for example, an average respiratory flow value, the absolute respiratory flow value remains below the predetermined respiratory flow value for a period of time after the respiratory volume begins to increase. As such, a portion of plot line portion 603 may be marked in the third plot line design. In such scenarios, the plot line can be retroactively corrected to eliminate the portion of plot line section 603 that is in the third plot line design. This correction is shown in FIG. 6D. When appropriately corrected, the apnea event is visualized on the graph via the presence of third plot line design only on plot line section 602 where the plot line is flat.

Figure 7A:
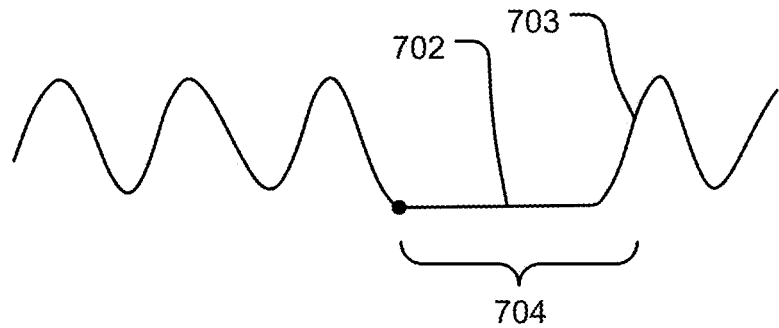
FIGS. 7A-7C are various views of a line plot illustrating respiratory volume as a function of time and various visualization options for low flow flags configured in accordance with various embodiments of the present technology.
Figure 7B:
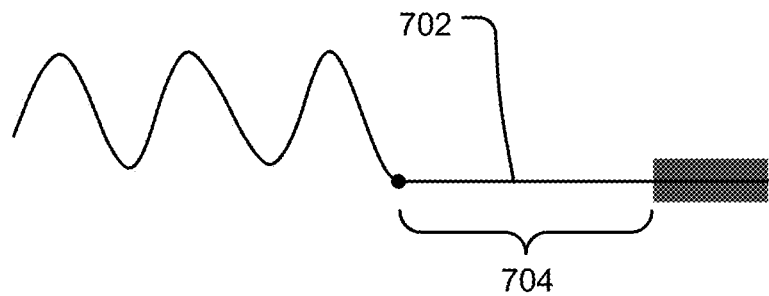
Figure 7C:
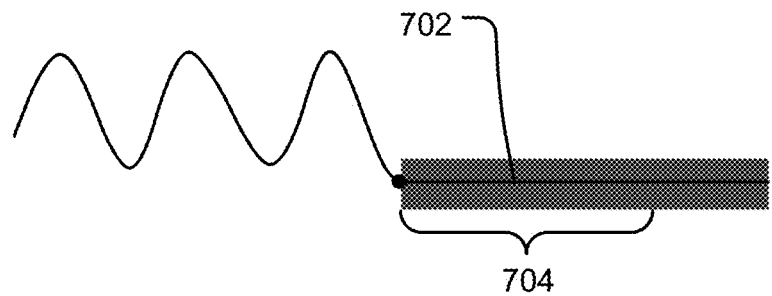

With reference to FIGS. 7A-7C, an embodiment where a predetermined period of time must be surpassed before any visual change to the plot line is carried out. While FIGS. 7A-7C generally illustrate application of this embodiment as it pertains to changing the plot line from the first plot line design to the second plot line design as discussed in greater detail with respect to FIGS. 5A-5C, it should be appreciated that this embodiment can also be applied to changing the plot line from the second plot line to the third plot line as discussed in greater detail with respect to FIGS. 6A-6D.

With reference to FIG. 7A, a graph illustrating changes in respiratory volume flow as a function of time is similar to the graphs previously discussed with respect to FIGS. 4-6A. As shown in FIG. 7A, the plot line section 702 is flat and therefore has an absolute respiratory flow value that is below the predetermined respiratory flow value. However, unlike in, for example, FIG. 5A, the plot line section 502 is not immediately visually changed from a first plot line design to a second plot line design based on the absolute respiratory flow value dropping below the predetermined respiratory flow value. Instead, plot line section 702 retains the first plot line design until it is determined that the absolute respiratory flow value remains below the predetermined respiratory flow value for longer than a predetermined period of time. As shown in FIG. 7A, the predetermined period of time 704 is not exceeded (i.e., the respiratory volume begins to increase at plot line section 703 before reaching the predetermined period of time 704), and therefore no visual change to plot line 701 is carried out.

With reference FIG. 7B, an embodiment in which the absolute respiratory flow value does remain below the predetermined respiratory flow value for longer than the predetermined period of time 704 is illustrated. In such an embodiment, the visual change of the plot line from the first plot line design to the second plot line design begins immediately after the predetermined period of time 704 is exceeded. In FIG. 7B, the portion of plot line section 702 prior to exceeding the predetermined period of time 704 is not retroactively converted to the second plot line design, but instead retains the first plot line design. In contrast, FIG. 7C illustrates an embodiment where retroactive correction of the plot line is carried out such that, once the plot line section 702 exceeds the predetermined period of time, all of plot line section 702 is converted to the second plot line design (i.e., both before and after the predetermined period of time).

The predetermined period of time 704 can be similar to the predetermined period of time as initially discussed previously with respect to FIG. 5B. That is to say, the predetermined period of time can be either fixed or dynamic, and a dynamic predetermined period of time can be calculated based on previously recorded patient data (e.g., an average time of the three preceding breaths multiplied by a multiplier). In some embodiments, regardless of whether the predetermined period of time is fixed or dynamic and regardless of the manner in which a dynamic predetermined period of time is calculated, the predetermined period of time used for determining when to initially change the plot line from a first plot line design to a second plot line design (i.e., upon identifying a low flow event) should be shorter than the predetermined period used to determine when to change the plot line from a second plot line design to a third plot line design (i.e., upon identifying an apnea event).

Figure 8:
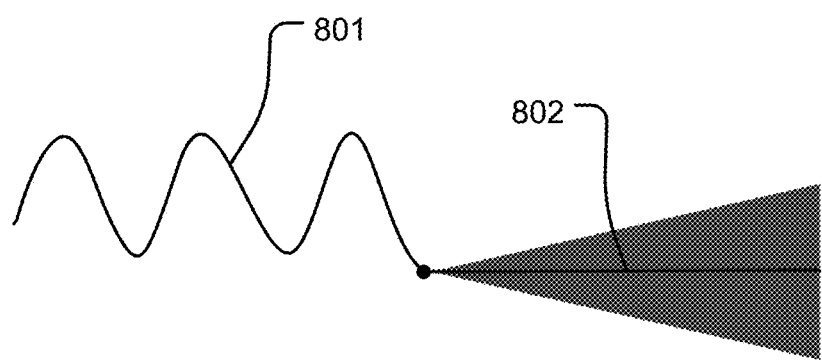
FIG. 8 is a line plot illustrating respiratory volume as a function of time and including a visualization showing a low flow flag configured in accordance with various embodiments of the present technology.

With reference to FIG. 8, the change from a first plot line design to a second plot line design and/or from a second plot line design to a third plot line design can be accompanied by an increase in intensity of the second plot line design or the third plot line design. For example, FIG. 8 illustrates a respiratory volume plot line 801 wherein the absolute respiratory flow value has dropped below a predetermined respiratory flow value, resulting in a change of the plot line from a first plot line design to a second plot line design at plot line section 802 (in this case from a thin blue line for the first plot line design to a yellow highlight overlaying the thin blue line for the second plot line design). FIG. 8 also illustrates how, as the absolute respiratory flow value remains below the predetermined respiratory flow value, the intensity of the second plot design at plot line section 802 line increases with the passage of time. The increase in intensity of the second plot line design is illustrated in FIG. 8 as the yellow highlight increasing in width. It should be appreciated, however, that any visual change in intensity can be used, including, but not limited to, a change in the thickness of the line, a change in the intensity of the color, or a change in color. FIG. 8 also illustrates a continuous, flowing change in intensity, but stepped or non-linear increases in intensity can also be used.

Figure 9:
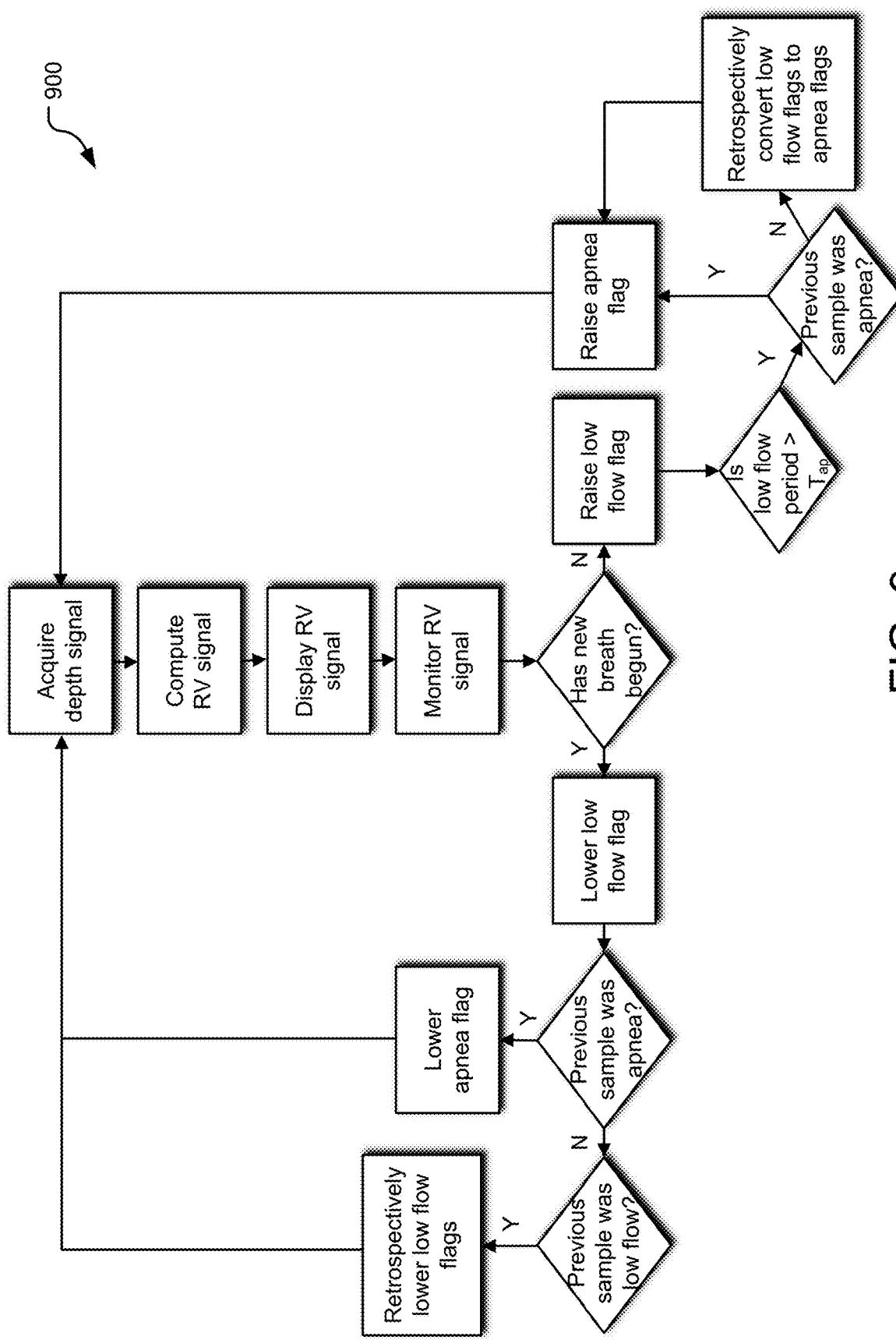
FIG. 9 is a flow chart of a method for providing an informative display of data obtained from non-contact monitoring of a patient configured in accordance with various embodiments of the present technology.

FIG. 9 illustrates an embodiment of a flow chart for carrying out the methods of providing informative display from non-contact patient monitoring as described in greater detail previously. The method 900 generally begins with a step 901 in which a depth signal is acquired, such as via a depth sensing camera having a region of interest of a patient in the field of view of the patient. In step 902, a respiratory volume value is calculated from the depth signals, such as through the use of a processor. In step 903, the calculated respiratory values are displayed on, for example, a display. The specific display of the respiratory volume values can include, in some embodiments, a graph with a plot line showing respiratory volume as a function of time. In step 904, the respiratory volume is continuously monitored so as to obtain continuous respiratory volume values that can be plotted as a rolling plot line on the graph displayed in step 903.

Step 905 represents a decision block in which it is determined whether or not the monitored patient has begun a new breath. The initiation of a new breath can be determined using, for example, the depth sensing camera monitoring the region of interest of the patient and from which breath information can be extrapolate. In the event that a new breath has begun, step 906 result in lowering a low flow flag (if present). The low flow flag can be lowered in this scenario because the presence of the new breath by the patient safely indicates that the patient is not experiencing a low flow event. Step 907 represents another decision block in which it is determined whether or not the previous data sample was identified as apnea. If the previous data sample had been identified as apnea, then the associated apnea flag is lowered at step 908. Again, it is possible to lower the apnea flag due to the previous identification of a new patient breadth. Following a lowering of the apnea flag at step 908, the flow chart may flow back to step 901. If the previous data sample had not been identified as apnea, then the flow chart proceeds to step 909, a decision block to determine if the previous data sample had been identified as a low flow. If the previous data sample had been identified as a low flow, then step 910 is carried out, in which the low flow flags are retroactively lowered. Following completion of step 910, the flow chart may flow back to step 901. While not shown in FIG. 9, if the decision block 909 is answered in the negative (i.e., previous data sample was not identified as low flow), then the flow chart may flow back to step 901.

Returning to decision block 905, if a new breath has not begun, the step 911 is performed in which a low flow flag is raised. Decision block 912 follows in which it is determined if the low flow period has exceeded the predetermined period of time (i.e., the period of time for establishing when an apnea event is occurring). While not shown in FIG. 9, if the answer is no (i.e., predetermined period of time has not been exceeded), then the flow chart flows back to step 901. If decision block 912 is answered in the affirmative, then decision block 913 follows in which it is determined if the previous data sample was labeled as apnea. If the answer is yes, then step 914 of raising the apnea flag is carried out, after which the flow chart flows back to step 901. If the answer is no (previous data sample was not apnea), then step 915 of retroactively converting the low flow flags to apnea flags is carried out. The flow chart then flows to step 914 to ensure the apnea flag has been raised, followed by reverting to step 901 of method 900.

Referring back to FIG. 3, an exemplary informative display 300 providing various information regarding a patient monitored by a non-contact patient monitoring system includes a patient depth image 310, a graph 320 detailing respiratory volume as a function of time, a histogram 330 tracking quantity of measured breathing rates within various breathing rate ranges, and a trend display 340 showing respiratory rate as a function of time. The display 300 may include any combination of these images, including adding additional images not discussed herein or omitting images discussed previously. Visualizations of various events, such as patient apnea events or patient motion events, can be added to one or more images 310, 320, 330, 340 of the informative display 300 to provide the clinician with additional aid in real time analysis or interpretation of patient monitoring data presented on the informative display 300.

Figure 10A:
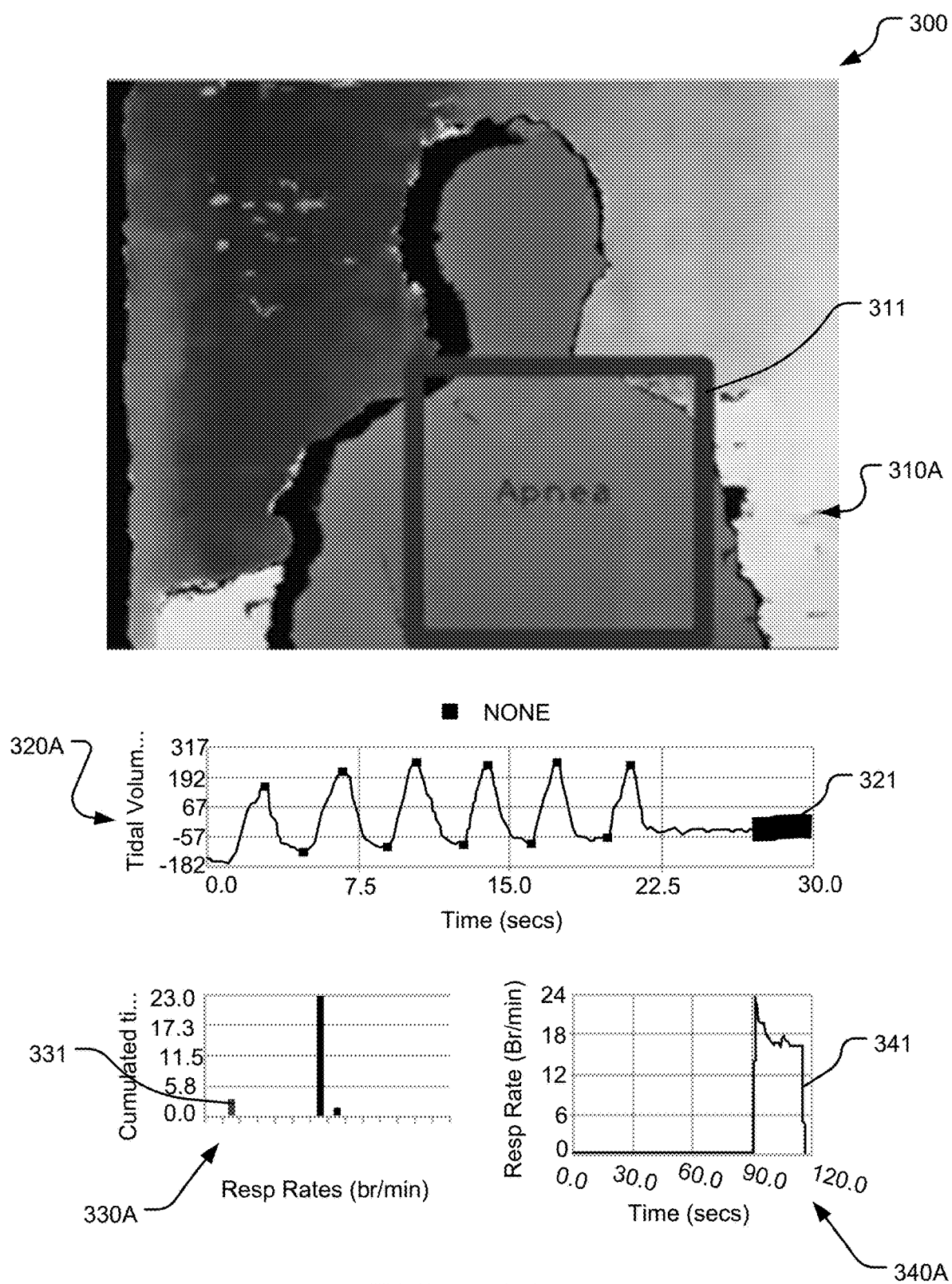
FIGS. 10A and 10B are display views for a video-based patient monitoring system configured in accordance with various embodiments of the present technology.
Figure 10B:
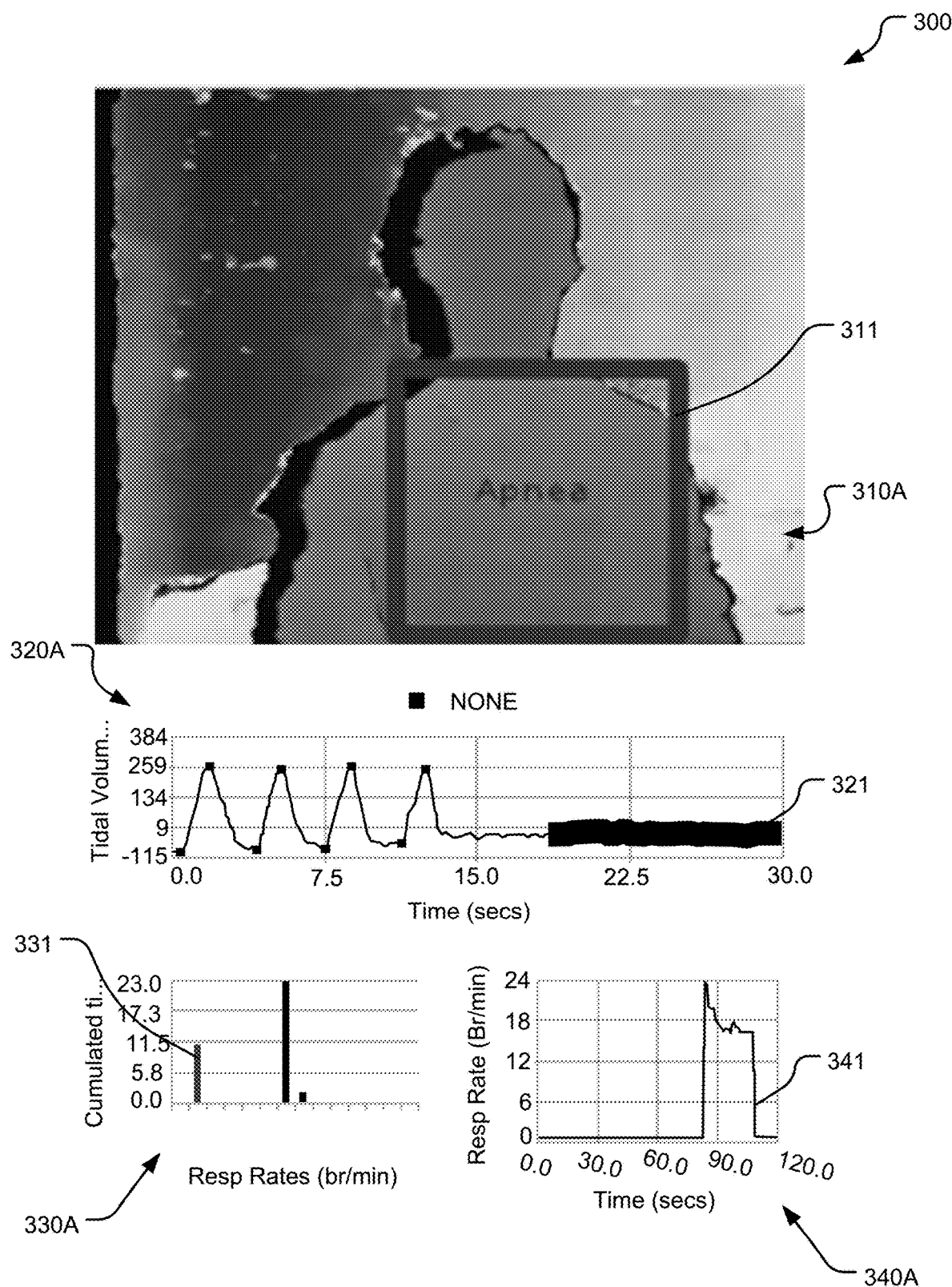

With reference to FIGS. 10A and 10B, a visual display 300 similar or identical to the visual display illustrated in FIG. 3 includes a patient depth image 310A, a graph 320A detailing respiratory volume as a function of time, a histogram 330A tracking quantity of measured breathing rates within various breathing rate ranges, and a trend display 340A showing respiratory rate as function of time. All of the data displayed in images 310A, 320A, 330A and 340A can be obtained and/or calculated from depth measurements obtained via depth sensing camera as described in greater detail above. All of images 310A, 320A, 330A and 340A also provide rolling patient data based on the continuous monitoring of the patient.

Each of images 310A, 320A, 330A, 340A are configured to provide additional visualizations of various patient events that are not necessarily immediately apparent or discernable from the basic data presented in images 310A, 320A, 330A and 340A. For example, and with respect to FIGS. 10A and 10B, additional visualizations are provided to more clearly convey to a clinician that an apnea event is occurring or has occurred. Apnea events can be determined via any suitable method, including any of the methods previously described, such as when the calculated absolute respiratory flow value falls below a predetermined respiratory flow value and remains below the predetermined respiratory flow value for longer than a predetermined period of time.

With respect to patient depth image 310A, a visualization 311 of the occurrence of an apnea event is provided by superimposing over the depth image a label, such as an "APNEA" label. As shown in FIGS. 10A and 10B, the visualization 311 can include a geometric shape, such as a square, inside of which the label is located. While FIGS. 10A and 10B show a label inside a geometric shape as the visualization 311 for an apnea event, it should be appreciated that any suitable visualization conveying the apnea event can be superimposed over the depth image during an apnea event. FIG. 10B shows the visual display 300 at a period of time after the visual display of FIG. 10A and during which the apnea event has continued. As shown in FIG. 10B, the visualization 311 has remained superimposed over the depth image 310A for the entire period of time of the apnea event. While not shown in FIG. 10B, in some embodiments, the visualization 311 can change as the duration of the apnea event grows longer. In some embodiments, the visualization 311 can begin to flash, grow larger, change color, etc., as the apnea event continues. A gradual or stepped increase in intensity as the apnea period continues can also be used. For example, the visualization 311 may initially appear as a static visualization at the start of the apnea event and remain as a static visualization until after a first predetermined period of time has elapsed. After the first predetermined period of time, the static visualization changes to a flashing visualization that may gradually increases in the speed of flashing as additional time in the apnea event elapses. Alternatively, the increase in flashing can be a stepped increase in flashing, with the speed of flashing increasing after the passing of each predetermined period of time.

With respect to graph 320A detailing respiratory volume as a function of time, the visualization of an apnea event may be similar or identical to the embodiments described previously wherein the design of the plot line changes once an apnea event has been determined and/or confirmed. As shown in FIGS. 10A and 10B, the plot line at section 321 visually changes to a plot line design different from the plot line design of the preceding portion of the plot line. The plot line section 321 with the different plot line design begins when an apnea event has been detected (e.g., when the absolute value of the respiratory flow value falls below and remains below a predetermined respiratory flow value for longer than a predetermined period of time). In the case of FIGS. 10A and 10B, the visual change in plot line design is from a thin black line design to a bold red line design, through it should be appreciated that any other change in plot line design can be used. FIG. 10B shows the visual display at a period of time after the visual display of FIG. 10A and during which the apnea event has continued. As such, the plot line section 321 with the different plot line design has elongated based on the different plot line design being maintained during the entirety of the apnea event. While not shown in FIG. 10B, the plot line design used for denoting the apnea event can change in intensity the longer the apnea event continues, such as through gradual or stepwise changes in flashing, color intensity, size, etc.

With respect to histogram 330A, the histogram 330A generally includes along the x-axis various ranges of breathing rates. For example, the various breathing rate ranges may include 0-4 breaths per minute (bpm), 5-8 bpm, 9-12 bpm, 13-16 bpm, etc. As the monitored patient exhibits various breathing rates, the bar over the associated breathing rate range within which the exhibited breathing rate occurred increases. As shown in FIG. 10A, the patient has exhibited breathing rates falling within predominantly one breathing rate range and therefore a bar associated with that breathing rate range is the largest of the bars included on the histogram 330A. As also shown in FIG. 10A, an apnea bar 331 has been added to the histogram as a visualization of the patient experiencing an apnea event. While the apnea bar 331 added to the histogram 330A is shown to the left of the lowest breathing rate range (e.g., 0 to 4 bpm), it should be appreciated that the apnea bar 331 may be positioned anywhere along the x-axis. In some embodiments, the apnea bar 331 has a different color from the other bars on the histogram, such as wherein the apnea bar 331 is red while the other bars are black.

As shown in FIG. 10B, the apnea bar 331 continues to grow as the apnea event continues. While not shown in FIG. 10B, the apnea bar 331 can visually change in intensity the longer the apnea event continues, such as through gradual or stepwise changes in flashing, color intensity, etc.

With respect to trend display 340A, the plot line 341 tracks the measured breaths per minute as a function of time. As shown in FIG. 10A, the monitored patient exhibits a breaths per minute rate in the range of 18 to 24 bpm during the time after patient monitoring has begun, followed by a sharp drop to zero when the apnea event occurs, with the drop to zero serving as the visualization of the apnea event in the trend display 340A portion of the visual display 300. As shown in FIG. 10B, the plot line 341 maintains at zero during as apnea event continues.

Any of the above described visualizations of an apnea event may be used alone or in any combination. Furthermore, any or all of the visualizations may be accompanied by an audible alarm that provides another signal of an apnea event. In some embodiments, the audible alarm begins immediately upon the start of the apnea event, while in other embodiments the audible alarm does not begin until after the apnea event has continued for longer than a predetermined period of time. The audible alarm may also increase in pitch and/or volume the longer the apnea event continues in order to convey to a clinician an increasing seriousness of apnea event.

Figure 11A:
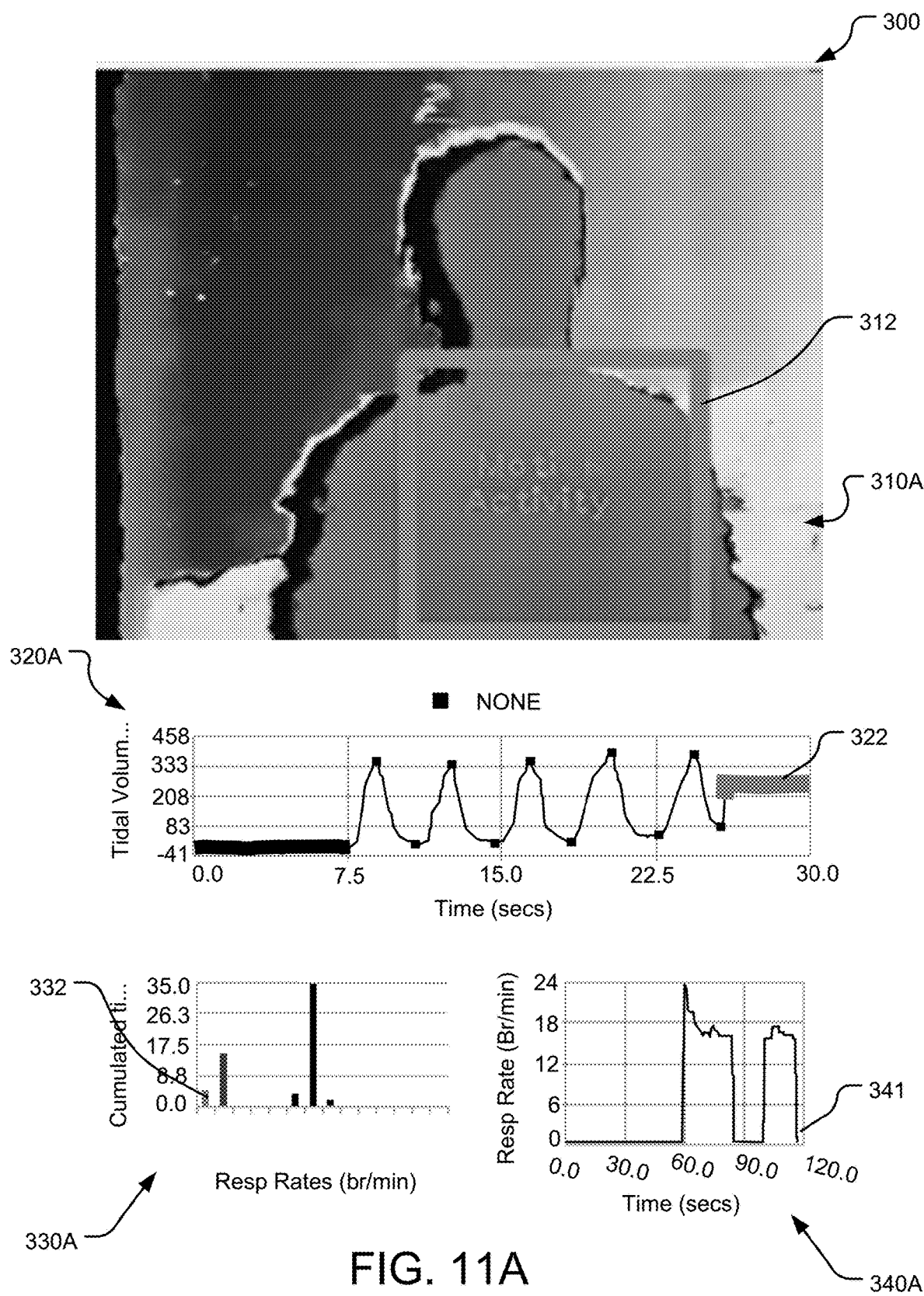
FIGS. 11A-11C are display views for a video-based patient monitoring system configured in accordance with various embodiments of the present technology.
Figure 11B:
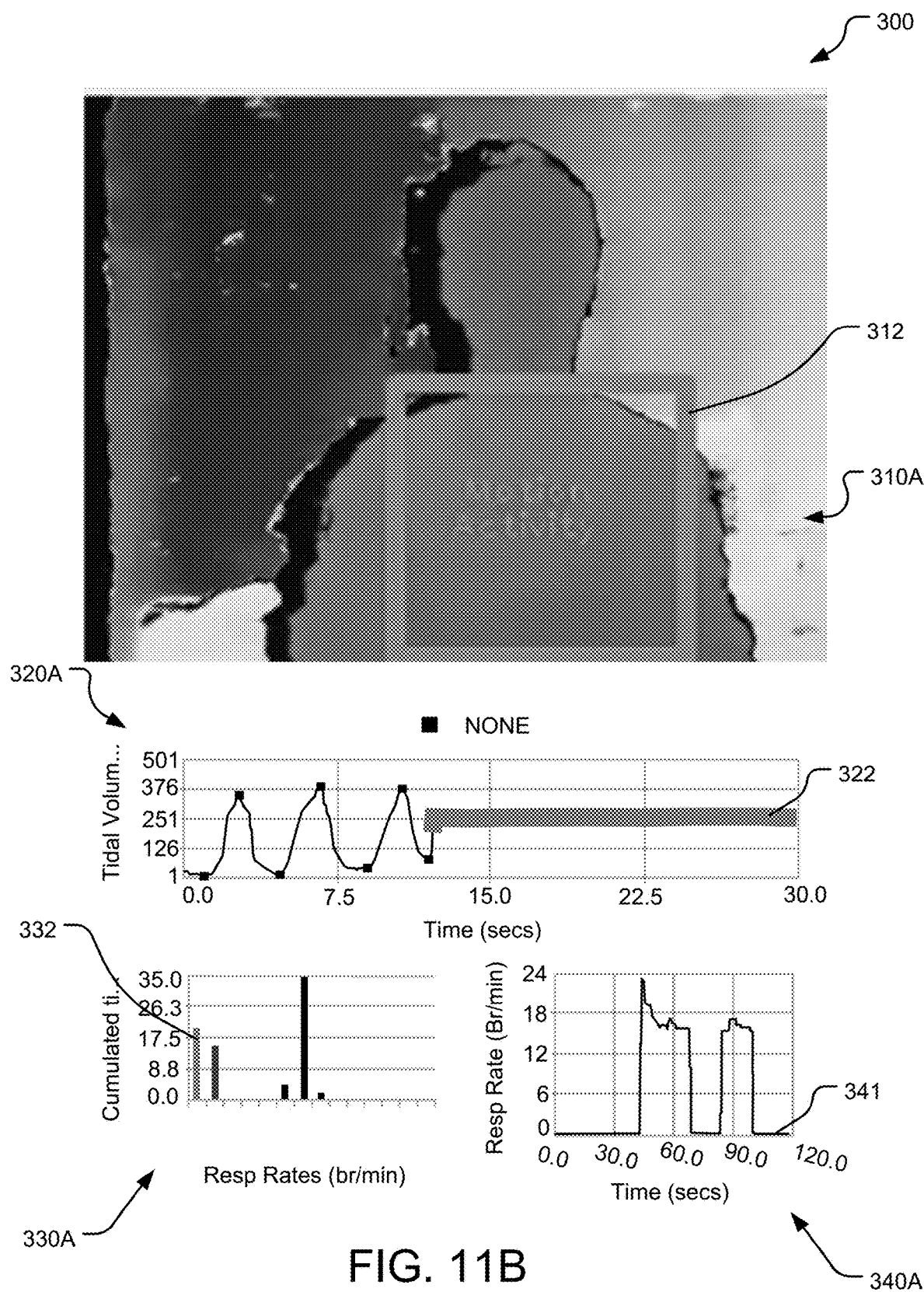

FIGS. 11A and 11B illustrate visualizations that can be similar to the visualizations used for apnea events as shown in FIGS. 10A and 10B, but which apply to patient motion events. The non-contact patient monitoring systems described herein and in related applications can detect patient motion via any suitable means or methods, such as when drastic changes in depth readings (i.e., larger changes than would be expected for patient breathing measurements) are obtained. When a patient being monitored by a non-contact monitoring system exhibits motion, it may be difficult to extract a high-quality respiratory volume signal and/or breathing information may not represent a clinically useful measure. For example, the clinician may want to collect breathing information pertaining only to an "at rest" patient rather than information that may be elevated when a patient is active. As such, the technology described herein may include embodiments where motion events are flagged so that clinicians may, for example, ignore and/or eliminate data collected during motion events.

In FIGS. 11A and 11B, patient depth image 310A may include a visualization 312 of a motion event that is provided by superimposing over the depth image 310A a label, such as a "MOTION" label. As shown in FIGS. 11A and 11B, the visualization 312 can include a geometric shape, such as a square, inside of which the label is located. While FIGS. 11A and 11B show a label inside a geometric shape as the visualization 312 for a motion event, it should be appreciated that any suitable visualization conveying the apnea event can be superimposed over the depth image during an apnea event. Furthermore, the visualization 312 for the motion event may be similar to the visualization 311 for the apnea event, or may have a completely different design so that it is easier for the clinician to discern between an apnea event and motion event.

FIG. 11B shows the visual display 300 at a period of time after the visual display of FIG. 11A and during which the motion event has continued. As shown in FIG. 11B, the visualization 312 has remained superimposed over the depth image 310A for the entire period of time of the motion event. While not shown in FIG. 11B, in some embodiments, the visualization 312 can change as the duration of the motion event grows longer. In some embodiments, the visualization 312 can begin to flash, grow larger, change color, etc., as the motion event continues. A gradual or stepped increase in intensity as the motion period continues can also be used. For example, the visualization 312 may initially appear as a static visualization at the start of the motion event and remain as a static visualization until after a first predetermined period of time has elapsed. After the first predetermined period of time, the static visualization changes to a flashing visualization that gradually increases in the speed of flashing as additional time in the motion event elapses. Alternatively, the increasing in flashing can be a stepped increase in flashing, with the speed of flashing increasing after the passing of each predetermined period of time.

With respect to graph 320A shown in FIGS. 11A and 11B and detailing respiratory volume as a function of time, the visualization of a motion event may generally include changing the design of the plot line beginning at the start of the motion event. As shown in FIGS. 11A and 11B, the plot line at section 322 visually changes to a plot line design different from the plot line design of the preceding portion of the plot line. The plot line section 321 with the different plot line design begins when a motion event has been detected. In the case of FIGS. 11A and 11B, the visual change in plot line design is from a thin black line design to a bold orange line design, through it should be appreciated that any other change in plot line design can be used. In some embodiments, the plot line design used to denote a motion event is different from the plot line design used to denote an apnea event. For example, FIG. 11A shows the bold red line from the previous apnea event and the bold orange line for the presently occurring motion event (separated by a thin bold line denoting normal breathing between the apnea event and the movement event).

FIG. 11B shows the visual display at a period of time after the visual display of FIG. 11A and during which the motion event has continued. As such, the plot line section 322 with the different plot line design has elongated based on the different plot line design being maintained during the entirety of the motion event. While not shown in FIG. 11B, the plot line design used for denoting the motion event can change in intensity the longer the motion event continues, such as through gradual or stepwise changes in flashing, color intensity, size, etc.

With respect to histogram 330A shown in FIGS. 11A and 11B, the histogram monitors the quantity of measured breathing rates within various ranges of breathing rates. As shown in FIG. 11A, a motion bar 332 has been added to the histogram as a visualization of the patient experiencing a motion event. The motion bar 332 is shown along with the previous added apnea bar 331 added to histogram 330A upon the occurrence of an apnea event. However, it should be appreciated that the motion bar 332 need not always be used in conjunction with an embodiment where an apnea bar 331 is added to the histogram 330A upon the occurrence of an apnea event (and vice versa). Similarly, while the motion bar 332 added to the histogram 330A is shown to the left of the lowest breathing rate range (e.g., 0 to 4 bpm) and the apnea bar 331, it should be appreciated that the motion bar 332 may be positioned anywhere along the x-axis. In some embodiments, the motion bar 332 has a different color from both the bars used for the breathing rates and the apnea bar 331, such as wherein the apnea bar 331 is red, the motion bar 332 is orange, and all other bars are black.

As shown in FIG. 11B, the motion bar 332 continues to grow as the motion event continues. While not shown in FIG. 11B, the motion bar 332 can visually change in intensity the longer the motion event continues, such as through gradual or stepwise changes in flashing, color intensity, etc.

With respect to trend display 340A shown in FIGS. 11A and 11B, the plot line 341 tracks the measured breaths per minute as a function of time. As shown in FIG. 11A, a sharp drop of the plot line 341 to zero occurs when the motion event begins, the drop to zero thereby serving as a visualization of the motion event in the trend display 340A portion of the visual display 300. As shown in FIG. 11B, the plot line 341 maintains at zero as the motion event continues.

While not shown in FIG. 11A or 11B, in another embodiment, the plot line 341 is held a constant value equal to the last breathing measurement taken before the motion event to provide the visualization of the motion event. In other words, rather than dropping to zero, the plot line flattens out and is held flat at the previously measured breathing rate for the duration of the motion event. An advantage of this embodiment may be that a different visualization is used on trend display 340A to differentiate between an apnea event (where the plot line 341 drops to zero) and a motion event (where the plot line 341 is maintained steady at the breathing rate value measured immediately prior to the start of the movement event). Changes in plot line design as described previously with respect to graph 320A can also be used in in trend display 340A, such as in conjunction with a drop to zero of the trend line or holding the trend line steady at the breathing rate measured immediately preceding the motion event.

Any of the above described visualizations of a motion event may be used alone or in any combination. Similarly, any combination of visualizations for apnea events and motion events can be used in the visual display 300. Furthermore, any or all of the previously described visualizations may be accompanied by an audible alarm that provides another signal of an apnea or a motion event. In some embodiments, an audible alarm for an apnea event or a motion event begins immediately upon the start of the associated event, while in other embodiments the audible alarm does not begin until after the event has continued for longer than a predetermined period of time. The audible alarm may also increase in pitch and/or volume the longer the event continues in order to convey to a clinician an increasing seriousness of event. In some embodiments, a different sound, pitch, pattern of sounds, etc., is used for each of an apnea event audible alarm and a motion event audible alarm.

As mentioned previously, breathing data collected during an identified motion event may be ignored and/or eliminated from breathing monitoring data used to determine various patient breathing parameters. For example, the processor used together with the non-contact patient monitoring system may be configured such that once a motion event is identified and for so long as the motion event is occurring, none of the breathing data collected is used in calculating any breathing parameter, such as respiratory volume or average breathing rates. In other embodiments, the data collected during a motion event is maintained and/or used in determining various patient breathing parameters. Any data from a motion event that is maintained can be incorporated with data from normal breathing events or used to create a separate data set of breathing parameters during motion events.

Figure 11C:
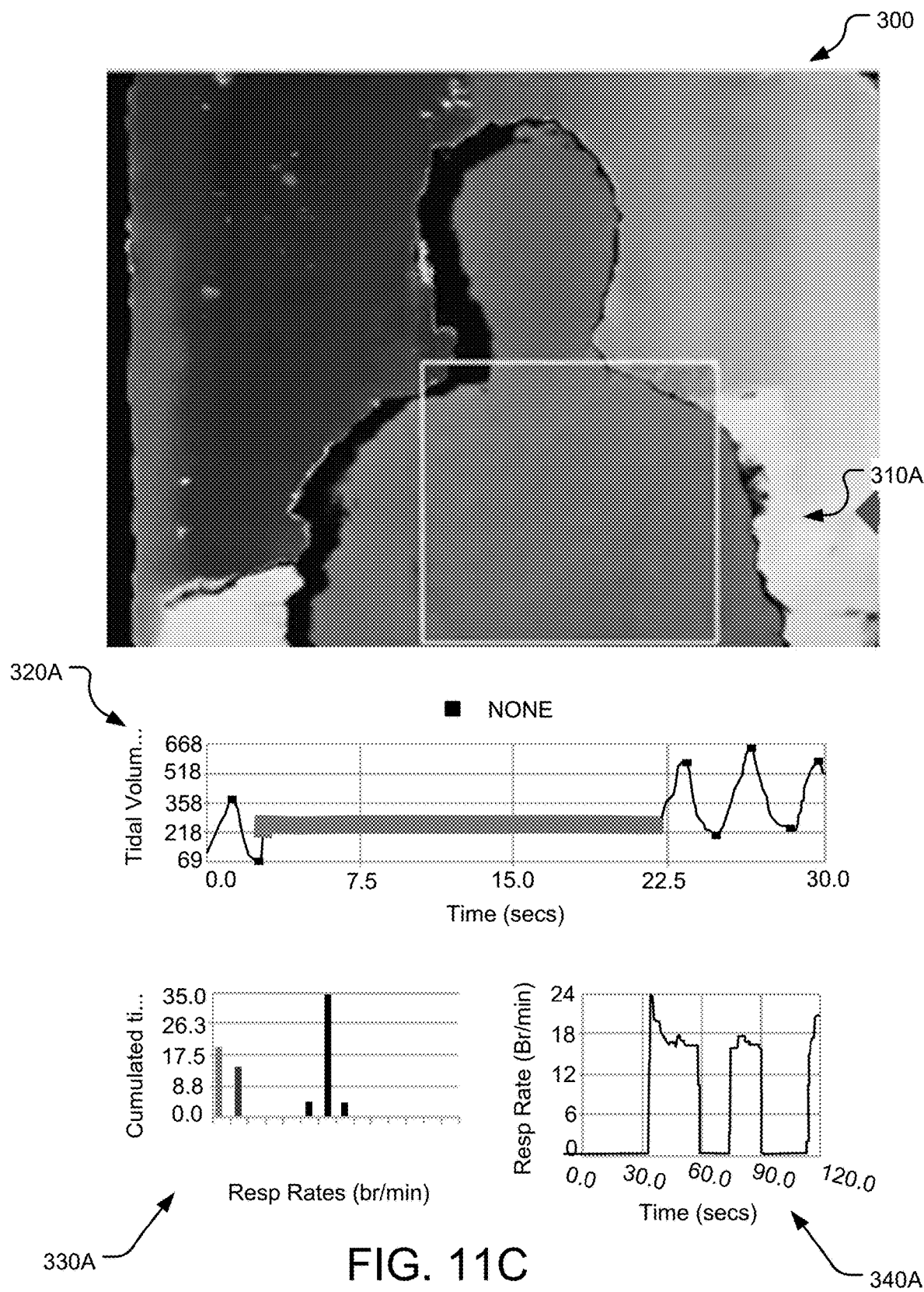

FIG. 11C shows visual display 300 after the motion event of FIGS. 11A and 11B has ended and normal breathing has returned. As shown in FIG. 11C, the visualizations 311 and 312 of FIGS. 11A and 11B have been removed from depth image 310A, the plot line in graph 320A has returned to its original plot line design, apnea bar 331 and movement bar 332 are no longer growing, and the plot line of trend display 340A has jumped up from the zero value used previously to denote an apnea or motion event. While FIG. 11C shows the visual display 300 after termination of a motion event, it should be appreciated that a similar change in the visual display 300 (e.g., removal of visualization 311 from depth image 310A, return to original plot line design in graph 320A, etc.) will occur upon termination of an apnea event.

Figure 12:
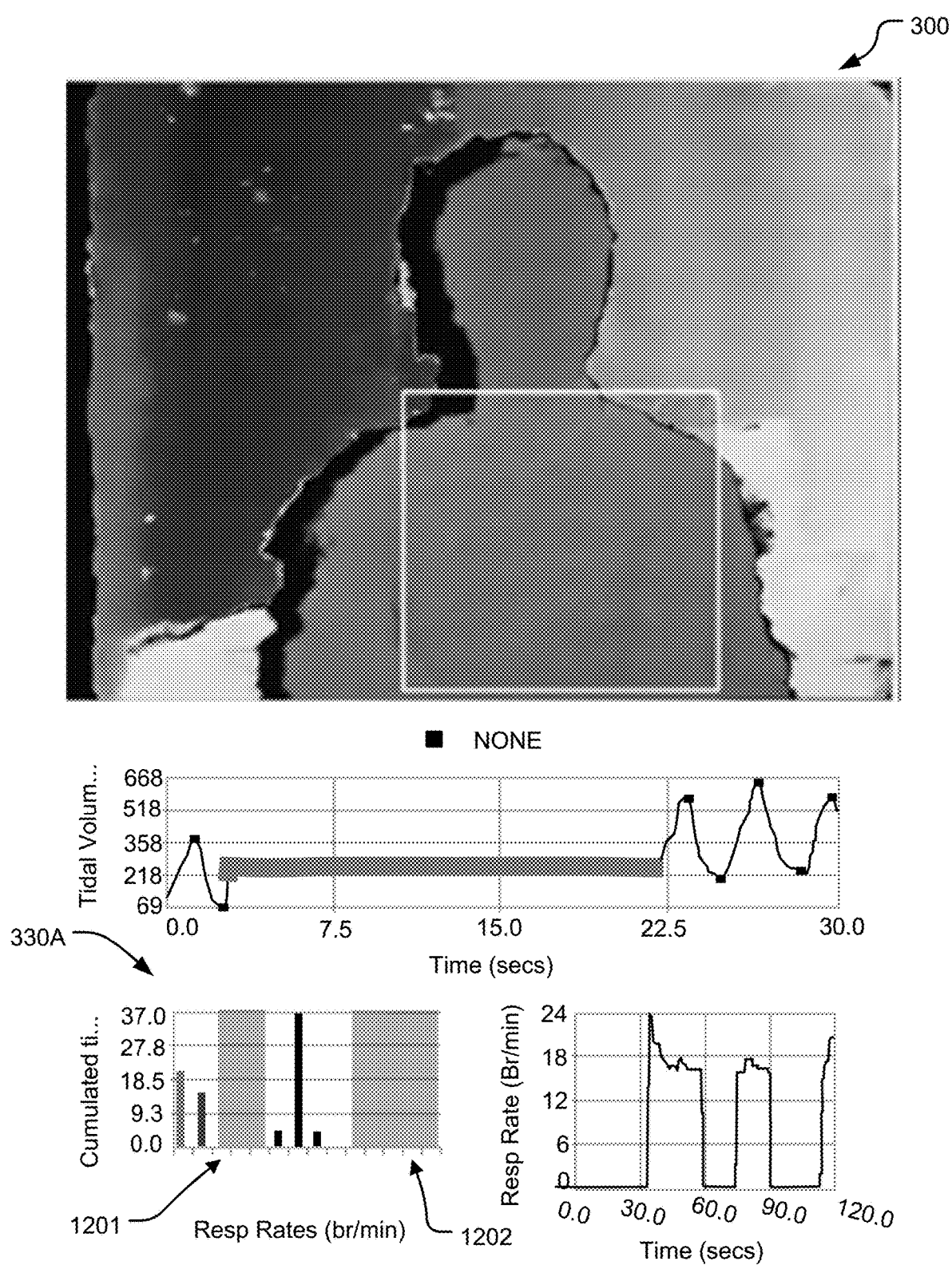
FIG. 12 is a display view for a video-based patient monitoring system configured in accordance with various embodiments of the present technology.

With reference to FIG. 12, another visualization change to the visual display 300 is presented, wherein the highest and lowest breathing rate measured for the patient is highlighted on histogram 330A. Thus, as shown in FIG. 12, the patient's lowest measured breathing rate is in the range of 0-4 bpm, and therefore highlight 1201 is added over that range on histogram 330A, while the patient's highest measured breathing rate is in the range of greater than 30 bpm, and therefore highlight 1202 is added over that range on histogram 330A. The addition of highlighted sections 1201, 1202 is dynamic such that should the lowest or highest breathing range measured change, the highlighted section 1201, 1202 moves to newly measured lowest or highest measured breathing rate. In another embodiment, predetermined low and high breathing rates are established and the breathing rate ranges below the predetermined low breathing rate are highlighted on histogram 330A (via highlight 1201), and the breathing rate ranges above the predetermined high breathing rate range are highlighted on histogram 330A (via highlight 1202). For example, a predetermined low breathing rate can be set at 8 bpm or lower, and a predetermined high breathing rate can be set at 24 bpm or higher, in which case the breathing rate ranges 0-4 bpm and 5-8 bpm are highlighted on histogram 330A, and breathing rate ranges 25-28 bpm, 29-32 bpm, and >32 bpm are highlighted on histogram 330A. With these breathing rate ranges now highlighted on histogram 330A, the clinician can easily identify when bars within these highlighted ranges are increasing.

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments can perform steps in a different order. Furthermore, the various embodiments described herein can also be combined to provide further embodiments.

The systems and methods described herein can be provided in the form of tangible and non-transitory machine-readable medium or media (such as a hard disk drive, hardware memory, etc.) having instructions recorded thereon for execution by a processor or computer. The set of instructions can include various commands that instruct the computer or processor to perform specific operations such as the methods and processes of the various embodiments described here. The set of instructions can be in the form of a software program or application. The computer storage media can include volatile and non-volatile media, and removable and non-removable media, for storage of information such as computer-readable instructions, data structures, program modules or other data. The computer storage media can include, but are not limited to, RAM, ROM, EPROM, EEPROM, flash memory or other solid-state memory technology, CD-ROM, DVD, or other optical storage, magnetic disk storage, or any other hardware medium which can be used to store desired information and that can be accessed by components of the system. Components of the system can communicate with each other via wired or wireless communication. The components can be separate from each other, or various combinations of components can be integrated together into a monitor or processor, or contained within a workstation with standard computer hardware (for example, processors, circuitry, logic circuits, memory, and the like). The system can include processing devices such as microprocessors, microcontrollers, integrated circuits, control units, storage media, and other hardware.

From the foregoing, it will be appreciated that specific embodiments of the technology have been described herein for purposes of illustration, but well-known structures and functions have not been shown or described in detail to avoid unnecessarily obscuring the description of the embodiments of the technology. To the extent any materials incorporated herein by reference conflict with the present disclosure, the present disclosure controls. Where the context permits, singular or plural terms can also include the plural or singular term, respectively. Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Where the context permits, singular or plural terms can also include the plural or singular term, respectively. Additionally, the terms "comprising," "including," "having" and "with" are used throughout to mean including at least the recited feature(s) such that any greater number of the same feature and/or additional types of other features are not precluded. Furthermore, as used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

We claim:

1. A video-based patient monitoring method, comprising:
   obtaining depth measurements within a region of interest using a depth-sensing camera;
   calculating respiratory volume values from the depth measurements using at least one processor;
   displaying a graph including a rolling plot line of the respiratory volume values as a function of time;
   calculating absolute respiratory flow from the rolling plot line using at least one processor;
   upon determining that the calculated absolute respiratory flow falls below a respiratory flow value, adapting the graph to indicate a low flow event, wherein adapting the graph comprises visually changing a section of the rolling plot line from a first plot line design to a second plot line design, the plot line section beginning at the time when the absolute respiratory flow initially fell below the respiratory flow value; and while continuing to indicate the low flow event, collecting additional respiratory volume data and adding the additional respiratory volume data to the graph;

subsequently adapting the graph to remove indication of the low flow event, comprising making a retroactive change to the plot line section, the retroactive change comprising removing the second plot line design from the plot line section and one of:

visually changing the plot line section to a third plot line design upon determining that the absolute respiratory flow remains below the respiratory flow value for longer than a benchmark period of time; and returning the plot line section to the first plot line design upon determining that the absolute respiratory flow crosses above the respiratory flow value prior to the benchmark period of time, and wherein the plot line designs include at least one of: color of the plot line, color intensity of the plot line, thickness of the plot line, a pattern of the plot line, shading of the plot line, size of the plot line, or flashing of the plot line.

2. The video-based patient monitoring method of claim 1, wherein the visual change to the plot line section from the second plot line design to the third plot line design applies retroactively to an entirety of the plot line section.

3. The video-based patient monitoring method of claim 1, wherein the returning the plot line section from the second plot line design to the first plot line design applies retroactively to an entirety of the plot line section.

4. The video-based patient monitoring method of claim 1, wherein the absolute respiratory flow is an average respiratory flow over a set period of time.

5. The video-based patient monitoring method of claim 4, wherein the third plot line design is maintained until the average respiratory flow rises above the respiratory flow value.

6. The video-based patient monitoring method of claim 5, wherein the set period of time is three seconds.

7. The video-based patient monitoring method of claim 5, wherein the rolling plot line visually changes from the third plot line design to the first plot line design after the average respiratory flow rises above the respiratory flow value.

8. The video-based patient monitoring method of claim 7, further comprising retroactively correcting the rolling plot line to remove the third plot line design and change to the first plot line design in a portion where the respiratory volume values begin to increase.

9. The video-based patient monitoring method of claim 1, wherein the benchmark period of time is a fixed value.

10. The video-based patient monitoring method of claim 1, wherein the benchmark period of time is a dynamic value.

11. The video-based patient monitoring method of claim 8, wherein the benchmark period of time is calculated based on an average breath duration over a set number of previous breaths.

12. The video-based patient monitoring method of claim 1, wherein the third plot line design increases in intensity the longer that the absolute respiratory flow remains below the respiratory flow value.

13. The video-based patient monitoring method of claim 8, wherein the plot line section having the third plot line design retains a historical visual presentation of an apnea event.

14. A video-based method of monitoring and displaying a patient's vital signs, comprising:
receiving depth measurements from a depth-sensing camera, the depth measurements being taken from within a region of interest;
calculating respiratory volume values from the depth measurements;
displaying on a display a graph including a rolling plot line of the respiratory volume values as a function of time;
calculating respiratory flow from the rolling plot line;
calculating an average respiratory flow over a set period of time;
displaying an indication of a low flow event by visually changing a section of the rolling plot line from a first plot line design to a second plot line design upon determining that the average respiratory flow falls below a respiratory flow value, the plot line section beginning at the time when the average respiratory flow initially fell below the respiratory flow value; and
subsequently performing one of:
upon determining that the average respiratory flow remains below the respiratory flow value for longer than a benchmark period of time, removing the indication of the low flow event and visually presenting an apnea event by retroactively changing an entirety of the plot line section to remove the second plot line design and change to a third plot line design
upon determining that the average respiratory flow rises above the respiratory flow value prior to the benchmark period of time, returning the plot line section to the first plot line design, and
wherein the plot line designs include at least one of: color of the plot line, color intensity of the plot line, thickness of the plot line, a pattern of the plot line, shading of the plot line, size of the plot line, or flashing of the plot line.

15. The video-based method of claim 14, further comprising:
visually changing the rolling plot line from the third plot line design to the first plot line design upon determining that the average respiratory flow rises back above the respiratory flow value, wherein the plot line section having the third plot line design retains a historical visual presentation of the apnea event.

16. The video-based method of claim 14, wherein the breath data comprises an average breath duration.

17. The video-based method of claim 14, further comprising displaying on the display a depth image and superimposing an apnea visualization over the depth image during the apnea event.

18. The video-based method of claim 14, wherein the benchmark period of time is dynamically calculated based on breath data preceding the apnea event.

19. A video-based patient monitoring method, comprising:
obtaining depth measurements within a region of interest using a depth-sensing camera;
calculating respiratory volume values from the depth measurements using at least one processor;
displaying a graph including a rolling plot line of respiratory volume values as a function of time;
calculating respiratory flow using at least one processor;
identifying a low flow event upon determining that the calculated respiratory flow falls below a respiratory flow value; and
adapting the graph to distinguish between ongoing analysis of the low flow event and classification of an apnea event, wherein adapting the graph comprises:
visually changing a section of the rolling plot line from a first design to a second design;
subsequently collecting additional respiratory volume data;

adding the additional respiratory volume data to the section in the second design;

upon determining that the respiratory flow remains below the respiratory flow value for longer than a benchmark period of time, retroactively removing the second design from the section and visually changing the section to a third design indicating the classification of the apnea event; and upon determining that the respiratory flow rises above the respiratory flow value after the benchmark period of time, visually changing the rolling plot line from the third design to the first design, such that the section having the third design retains a historical visual presentation of the apnea event, and wherein the plot line designs include at least one of: color of the plot line, color intensity of the plot line, thickness of the plot line, a pattern of the plot line, shading of the plot line, size of the plot line, or flashing of the plot line.

20. The video-based patient monitoring method of claim 19, further comprising retroactively correcting the graph to remove the third design and change to the first design in a portion of the rolling plot line where the respiratory volume values begin to increase.

* * * * *